US009845506B2

(12) United States Patent
Lorincz et al.

(10) Patent No.: US 9,845,506 B2
(45) Date of Patent: Dec. 19, 2017

(54) METHOD FOR DETERMINING PROGNOSIS OF PROSTATE CANCER IN A SUBJECT

(71) Applicant: Queen Mary University of London, London (GB)

(72) Inventors: Attila Lorincz, Charterhouse Square (GB); Natasa Vasiljevic, Charterhouse Square (GB); Amar Ahmad, Charterhouse Square (GB)

(73) Assignee: Queen Mary University of London, London (GB)

( * ) Notice: Subject to any disclaimer, the term of this patent is extended or adjusted under 35 U.S.C. 154(b) by 0 days.

(21) Appl. No.: 14/386,292

(22) PCT Filed: Mar. 19, 2013

(86) PCT No.: PCT/GB2013/050714
§ 371 (c)(1),
(2) Date: Sep. 18, 2014

(87) PCT Pub. No.: WO2013/140161
PCT Pub. Date: Sep. 26, 2013

(65) Prior Publication Data
US 2015/0051084 A1 Feb. 19, 2015

(30) Foreign Application Priority Data

Mar. 19, 2012 (GB) .................................. 1204785.8

(51) Int. Cl.
*C07H 21/04* (2006.01)
*C12Q 1/68* (2006.01)

(52) U.S. Cl.
CPC ...... *C12Q 1/6886* (2013.01); *C12Q 2600/118* (2013.01); *C12Q 2600/154* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2001/0053519 A1* 12/2001 Fodor .................. B01J 19/0046
435/6.11
2008/0254447 A1* 10/2008 Foekens ............... C12Q 1/6886
435/6.14

FOREIGN PATENT DOCUMENTS

| EP | 2737913 B1 | 6/2016 |
|----|-----------|--------|
| WO | WO2004030660 | 4/2004 |
| WO | 2004/030660 A2 | 6/2004 |
| WO | 2005/059172 A2 | 6/2005 |
| WO | WO2005059172 | 6/2005 |
| WO | 2006/092610 A2 | 9/2006 |
| WO | WO2006092610 | 9/2006 |
| WO | 2012168532 A1 | 12/2012 |

OTHER PUBLICATIONS

NEB catalog (1998/1999), pp. 121, 284.*
Genbank Accession No. DJ059987 (Jan. 2008).*
Accession No. DJ059987, EMBL Online Database.
Banez, et al., Multicenter clinical validation of PITX2 methylation as a prostate specific antigen recurrence predictor in patients with post-radical prostatectomy prostate cancer, J. Urol. (2010) 184:149-156.
Bastian, et al., Molecular biomarker in prostate cancer: the role of CpG island hypermethylation, Eur. Urol. (2004) 46:698-708.
Benjamini, et al., Controlling the false discovery rate: a practical and powerful approach to multiple testing, Journal of the Royal Statistical Society (1995) 57:289-300.
Berdasco, et al., Aberrant epigenetic landscape in cancer: how cellular identity goes awty, M. Dev Cell (2010) 19:698-711.
Berney, et al., Ki-67 and outcome in clinically localised prostate cancer: analysis of conservatively treated prostate cancer patients from the Trans-Atlantic Prostate Group study, Br J Cancer (2009) 100:888-93.
Buchner, Supervising the fold: functional principles of molecular chaperones, FASEB (1996) 10:10-9.
Cedar, et al., Linking DNA methylation and histone modification: patterns and paradigms, Nat Rev Genet (2009) 10:295-304.
Chang, et al., Promoter methylation of heat shock protein B2, Int. J. Oncol. (2011) 38:1129-1135.
Chung, et al., Identification of novel tumor markers in prostate, colon and breat cancer by unbiased methylation profiling, PLoS One (2008) 3(4):e2079.
Cornford, et al., Heat shock protein 27 increases after androgen ablation and plays a cytoprotective role in hormone-refractory prostate cancer, Cancer Res. (2004) 64:6595-602.
Cuzick, et al., Long-term outcome among men with conservatively treated localised prostate cancer, Br. J. Cancer (2006) 951186-94.
Cuzick, et al., Prognostic value of an RNA expression signature derived from cell cycle proliferation genes in pateints with prostate cancer: a retrospective study, Lancet Oncol (2011) 12:245-55.
Ellinger, et al., The role of cell-free circulating DNA in the diagnosis and prognosis of prostate cancer, Urol. Oncol. (2009) 29:124-129.
Epstein, et al., The 2005 International Society of Urological Pathology (ISUP) consensus conference on Gleason grading of prostatic carcinoma, Am. J. Surg. Pathol. (2005) 29:1228-42.
Foster, et al., Hsp-27 expression at diagnosis predicts poor clinical outcome in prostate cancer independent of ETS-gene rearrangement, Br. J. Cancer (2009) 101:1137-1144.
Foster, et al., Urgent need to develop independent biomarkesr for functional, diagnostic, and prognostic application in oncology research, Biomark Med. (2009) 3:329-333.
Garrido, et al., Heat shock proteins 27 and 70, anti-apoptotic proteins with tumorigenic properties, Cell Cycle (2006) 5:2592-601.

(Continued)

*Primary Examiner* — Jeanine A Goldberg
(74) *Attorney, Agent, or Firm* — Stradley Ronon Stevens & Young, LLP

(57) ABSTRACT

A method for determining the prognosis of prostate cancer in a subject is provided which comprises the assessment of the methylation status of the HSPB1 gene in a prostate cancer sample.

8 Claims, 15 Drawing Sheets

(56) References Cited

OTHER PUBLICATIONS

Figure 1A:
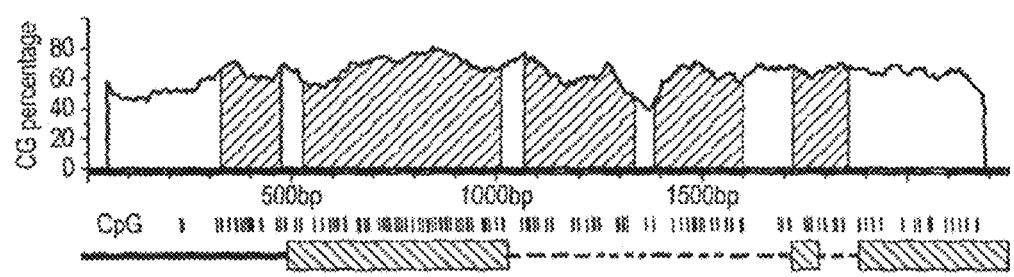

Garrido, et al., Heat shock proteins: endogenous modulators of apoptotic cell death, Biochem Biophys Res Commun (2001) 286:433-42.

Geisler, et al., HSP27 in patients with ovarian carcinoma: still an independent prognostic indicator at 60 months follow-up, Eur. J. Gynaecol. Oncol. (2004) 25:165-8.

Glasessgen, et al., Heat shock proteins 27, 60 and 70 as prognostic markers of prostate cancer, APMIS (2008) 116 (10):888-895.

Gleason, et al., Prediction of prognosis for prostatic adenocarcinoma by combined histological grading and clinical staging, J. Urol. (1974) 111:58-64.

Glinsky, et al., Gene expression profilling predicts clinical outcome of prostate cancer, J. Clin. Invest (2004) 113:913-923.

Graceffa, Hsp27-Actin interaction, P. Biochem Res. Int. (2011) 901572.

Henrique, et al., High promoter methylation levels of APC predict poor prognosis in sextant biopsies from prostate cancer patients, Clin. Cancer Res. (2007) 13:6122-6129.

Herman, et al, Gene silencing in cancer in association with promoter hypermethylation, N. Eng. J. Med. (2003) 349:2042-54.

Hessels, et al., Applicability of biomarkers in the early diagnosis of prostate cancer, Expert Rev Mol Diagn (2004) 4:513-26.

Hickey, et al., Sequence and organization of genes encoding the human 27 kDa heat shock protein, Nucleic Acids Res (1986) 14:4127-45.

Homo sapiens chromosome 12, NCBI Reference Sequence: NC_000012.11 version GI 224589803.

Homo sapiens chromosome 8, NCBI Reference Sequence: NC_000008.10 version GI 224589820.

International Human Genome Sequencing Consortium (IHGSC), Finishing the euchromatic sequence of the human genome, Nature (2004) 431(7011):931-945.

International Human Genome Sequencing Consortium (IHGSC), Initial sequencing and analysis of the human genome, Nature (2001) 409(6822):860-921.

Kagan, et al., Towards clinical application of methylated DNA sequences as cancer biomarkers: a joint NCI's EDRN and NIST workshop on standards, methods, assays, reagents, and tools, Cancer Res (2007) 67:4545-4549.

Li, et al., MethPrimer: designing primers for methylation PCRs, Bioinformatics (2002) 18:1427-31.

Lin, et al., Indentification of candidate prostate cancer biomarkers, Int. J. Cancer (2007) 121:2596-2605.

Lindquist, et al., The heat-shock proteins, Annu Rev Genet (1988) 22:631-77.

Liu, et al., Association of tissue promoter methylation levels of APC, TGFβ2, HOXD3, and RASSF1A with prostate cancer progression, Int J Cancer (2011) 129:2454-2462.

Majumdar Sunipa, et al., Aberrant DNA methylation and prostate cancer, Current Genomics (2011) 12(7):486-505.

Mao, et al., Distinct genomic alterations in prostate cancers in Chinese and wester npopulations suggests alternative pathways of prostate carcinogenesis, Cancer Res (2010) 70:5207-5212.

McShane, et al., REorting recommendations for tumor MARKer prognostic studies (REMARK), Breast Cancer Res Treat (2006) 100:229-235.

Mehra, et al., Characterization of TMPRSS2-ETS gene aberrations in androgen-independent metastatic prostate cancer, Cancer Res (2008) 68:3584-90.

Moore, et al., Population-based prostate-specific antigen testing in the UK leads to a starge migration of prostate cancer, BJU Int (2009) 104:1592-8.

Morino, et al., Specific expression of HSP27 in human tumor cell lines in vitro, In Vivo (1997) 11:179-84.

Nelson, et al., Abnormal DNA methylation, epigenetics, and prostate cancer, Front Biosci (2007) 12:4254-4266.

Nguyen, et al., Susceptibilty of nonpromoter CpG islands to de novo methylation in normal and neoplastic cells, J Natl Cancer Inst (2001) 93:1465-72.

Nusbaum et al., DNA sequence and analysis of human chromosome 8, Nature (2006) 439(7074):331-335.

O'Brien, et al., Evaluation of prediagnostic prostate-specific antigen dynamics as predictors of death from prostate cancer in patients treated conservatively, Int J Cancer (2011) 10:2373-81.

Oesterreich, et al., Basal regulatory promoter elements of the hsp27 gene in human breast cancer cells, Biochem Biophys Res Commun (1996) 222:155-63.

Ono, et al., Overexpression of heat shock protein 27 in squamous cell carcinoma of the uterine cervix: a proteomic analysis using acrchival formalin-fixed, paraffin-embedded tissues, Hum Pathol (2009) 40:41-49.

Parkin, et al., Cancer incidence in five continents vol. VIII, IARC scientific publication No. 155 (2002).

Glaessgen, A. et al., "Heat shock proteins 27, 60 and 70 as prognostic markers of prostate cancer", APMIS, 2008, 116 (10):888-895.

Madjumdar, S. et al., "Aberrant DNA methylation and prostate cancer", Current Genomics, 2011, 12(7):486-505.

Database EMBL (Online), Jan. 16, 2008, Database accession No, DJ059987.

Vasiljevic, N, et al. "Association between DNA methylation of HSPB1 and death in low Gleason score prostate cancer", Prostate Cancer and Prostatic Diseases, 2013, 16(1):35-40.

Chang, X. et al., "Promoter methylation of heat shock protein B2 in human esophageal squamous cell carcinoma", International Journal of Oncology, 2011, 38:1129-1135.

Foster, C.S. et al., "Hsp-27 expression at diagnosis predicts poor clinical outcome in prostate cancer independent of ETS-gene rearrangement", British Journal of Cancer, 2009, 101:1137-1144.

Lin, J. et al., "Identification of candidate prostate cancer biomarkers in prostate needle biopsy specimens using proteomic analysis", International Journal of Cancer, 2007, 121:2596-2605.

Phe, et al., Methylated genes as potential biomarkers in prostate cancer, BJU Int (2010) 105:1364-1370.

Richiardi, et al., Promoter methylation in APC, RUNx3, and GSTP1 and mortality in prostate cancer patients, J Clin Oncol (2009) 27(9):3161-3168.

Rocchi, et al., Heat shock protein 27 increases after androgen ablation and plays a cytoprotective role in hormone-refractory prostate cancer, Cancer Res (2004) 64:6595-602.

Rosenbaum, et al., Promoter hypermethylation as an independent prognostic factor for relapse in patients with prostate cancer following radical prostatectomy, Clin Cancer Res (2005) 11:8321-8325.

Sakai, et al., Allele-specific hypermethylation of the retinoblastoma tumor-suppressor gene, Am. J. Hum. Genet. (1991) 48:880-888.

Scherer, et al., The finished DNA sequence of human chromosome 12, Nature (2006) 440(7082):346-351.

Schroder, et al., Screening and prostate-cancer mortality in a randomized european study, N. Engl. J. Med. (2009) 360:1320-1328.

Stamey, et al., Prostate-specific antigen as a serum marker for adenocarcinoma of the prostate, N. Engl. J. Med. (1987) 317:909-916.

Thanner, et al., Heat shock protein 27 is associated with decreased survival in node-negative breast cancer patients, Anticancer Res (2005) 25:1649-1653.

van Poppel, et al., The relationship between prostate cancer gene 3 (PCA3) and prostate cancer significance, BJUI (2012) 109:360-366.

Vanaja, et al., Hypermethylation of genes for diagnosis and risk stratification of prostate cancer, Cancer Invest. (2009) 27(5):549-560.

Vasiljevic, et al., Absolute quantitation of DNA methylation of 28 candidate genes in prostate cancer using pyrosequencing, Disease Markers (2011) 30:151-161.

Vasiljevic, et al., Association between DNA methylation of HSPB1 and death in low Gleason score prostate cancer, Prostate Cancer and Prostatic Diseases (2013) 16(1):35-40.

(56) References Cited

OTHER PUBLICATIONS

Ya, et al., PRKC-ξ expression promotes the aggressive phenotype of human prostate cancer cells and is a novel target for therapeutic intervention, Genes & Cancer (2010) 1:444-464.
Zoubeidi, et al., Hsp27 promoted insulin-like growth factor-1 survival signaling in prostate cancer via p90Rsk-dependent phosphorylation and inactivation of BAD, Cancer Res (2010) 70:2307-2317.
Canine et al., Development of recombinant cationic polymers for gene therapy research, Advanced Drug Delivery Reviews 2010 62(15):1524-9.
Castelletto et al., Modulating self-assembly of a nanotape-forming peptide amphiphile with an oppositely charged surfactant, Soft Matter 2012 8(1):217.
Keeley et al., Elastin as a self-organizing biomaterial: use of recombinantly expressed human elastin polypeptides as a model for investigations of structure and self-assembly of elastin, Philosophical Transactions of the Royal Society of London Biological Sciences 2002 357(1418):185-9.
Official Action dated Jan. 26, 2017 from related U.S. Appl. No. 14/655,090.
Smith et al., J. Tissue Eng. Regen. Med., 2012, 6(Supp.1):1-429.
dictionary.com, http://www.dictionary.com/browse/membrance, access on Jan. 21, 2017.
Non-final Office Action dated Sep. 7, 2017 issued in related U.S. Appl. No. 14/655,090.
Zhou et al., "Silk Fibroin:Structural Implications of a Remarkable Amino Acid Sequence", Proteins: Structure, Function, and Genetics, 2001, 44, pp. 119-122.

\* cited by examiner

SEQ ID NO: 7 – HSBP1 gene sequence

```
1 -    tgcccagact ggtctcaaac tcctagcctc aagggaccct tctgccttgg
51 -   cctcccaaag tgctgagatt acaggcatga gccatgcacc cagcccttt
101 -  ttaaaatttt tttgagagac aagactttga tctgttgcct aggctggagt
151 -  gcagtggtga gatcatagct cactgcagcc tcaactcctg ggctcaagca
201 -  ccagactcct tttatcacat tctatctcac acgcgtgtgg ttccaatcct
251 -  gcctctgcca ctctcagtt gtatgcccca acccaacctg tctggctctg
301 -  tcctccttaa cagaaggacg gccctggcca cgggcacag ccagcaacgc
351 -  ttaagcacca gggccggcga gtgccctgcc gtggcacggc tccagcgtcg
401 -  cgctctcgaa ttcatttgct ttccttaacg agagaaggtt ccagatgagg
451 -  gctgaaccct cttcgccccg cccacggccc ctgaacgctg ggggaggagt
501 -  GCATGGGGAG GGGCGGCCCT CAAACGGGTC ATTGCCATTA ATAGAGACCT
551 -  CAAACACCGC CTGCTAAAAA TACCCGACTG GAGGAGCATA AAGCGCAGC
601 -  CGAGCCCAGC GCCCCGCACT TTTCTGAGCA GACGTCCAGA GCAGAGTCAG
651 -  CCAGCATGAC CGAGCGCCGC GTCCCCTTCT CGCTCCTGCG GGGCCCCAGC
701 -  TGGGACCCCT TCCGCGACTG GTACCCGCAT AGCCGCCTCT TCGACCAGGC
751 -  CTTCGGGCTG CCCCGGCTGC CGGAGGAGTG GTCGCAGTGG TTAGGCGGCA
801 -  GCAGCTGGCC AGGCTACGTG CGCCCCCTGC CCCCCGCCGC CATCGAGAGC
851 -  CCCGCAGTGG CCGCGCCCGC CTACAGCCGC GCGCTCAGCC GGCAACTCAG
901 -  CAGCGGGGTC TCGGAGATCC GGCACACTGC GGACCGCTGG CGCGTGTCCC
951 -  TGGATGTCAA CCACTTCGCC CCGGACGAGC TGACGGTCAA GACCAAGGAT
1001 - GGCGTGGTGG AGATCACCGg tgagccccc tgctcctgca ggggagagga
1051 - ggaggctagc agggcgggca gggccggggg cgtgcggtg aaacgggggt
1101 - cccggggggcc tggggagtta aacgttggcc cagcaccggg aaaaascagga
1151 - ctcctgattc ccttgctcag gaattgggag tgcgggtcgc ttctaagggc
1201 - gctttctgct ctgtaatccc agcgcttgg gaggccgaga cgggaggatc
1251 - gcttgaggcc aggagttcaa gactagcctg ggcaacatag cgagacgcgc
1301 - ccccccgccc cgacccgcg ccattacaaa aaaaaagcaa acaaaaattt
1351 - ttttaaagat catcgatgaa gagagaaaat gcgctttct acagagtccc
1401 - cttcccaccc acagcccat cccagataa gcggggagtt ccctggcgcg
1451 - gtgccagttt ctagccgctg agtgggcgtg tgcgcggctc caagtgcgcc
1501 - tgcgtactgc tcactcccca gctccgcgcc ctgctccgtt cctcccaaaa
1551 - ctctgaatcg aagaactttc cggaagtttc tgagagccca gaccggcggg
1601 - cacgccccca tccccaaccc cctctgttaa tccctaccag cctgcagtcc
1651 - tggctgcttcc aagcaggagg tggggcctct ggcctagcgg gccgaaag
1701 - gcagtcccct ccccccgcagt ctgattcccc tcttccccccc aaagGCAAGC
1751 - ACGAGGAGCG GCAGGACGAG CATGGCTACA TCTCCCGGTG CTTCACGCGG
1801 - AAATACACGt gagtcctggc gccaggtcgg ggtgggtggg tggcgtgggg
1851 - gtggggtcag ggaagagggc acagggaccc acccggtgtg taatgtaacg
1901 - cttgccttc ctctctgcac gtccagGCTG CCCCCCGGTG TGGACCCCAC
1951 - CCAAGTTTCC TCCTCCCTGT CCCCTGAGG GCACACTGAC CGTGGAGGCCC
2001 - CCATGCCCAA GCTAGCCACG CAGTCCAACG AGATCACCAT CCCAGTCACC
2051 - TTCGAGTCGC GGGCCCAGCT TGGGGGCCCA GAAGCTGCAAA ATCCGATGA
2101 - GACTGCCGCC AAGTAAAGCC TTAGCCCGGA TGCCCACCCC TGCTGCCGCC
2151 - ACTGGCTGTG CCTCCCCCGC CACCTGTGTG TTCTTTTGAT ACATTTATCT
2201 - TCTGTTTTTC TCAAATAAAG TTCAAAGCAA CCACCTGTCA
```

FIG. 5

METHOD FOR DETERMINING PROGNOSIS OF PROSTATE CANCER IN A SUBJECT

The present application relates to methods of determining the prognosis for subjects with prostate cancer.

Heat shock protein (Hsp)-27, encoded by the gene HSPB1, belongs to a family of chaperone proteins and is a major regulator of numerous homeostatic pathways, protecting the cell from heat, irradiation and oxygen radicals (Garrido et al Biochem Biophys Res Commun, 286: 433-42, 2001). Constitutively expressed in most human cells (Lindquist, S., and Craig, E. A. Annu Rev Genet, 22: 631-77, 1988) Hsp-27 is strongly induced by cellular stress. Following induction, in addition to preventing protein aggregation (Buchner, J. FASEB J, 10:10-9, 1996), Hsp-27 interferes with caspase activation and inhibits apoptosis through multiple protein interactions allowing cellular homeostasis (Garrido et al Cell Cycle, 5: 2592-601, 2006). Overall this event is beneficial to the organism since it promotes cellular repair and recovery. However it may also be detrimental because high levels of anti-apoptotic proteins contribute to increased survival of carcinogenic cells. Furthermore, Hsp-27 expression is induced by hormone- or chemotherapy and inhibits treatment-induced apoptosis (Zoubeidi et al Cancer Res, 70: 2307-17, 2010). Accordingly, it is not surprising that studies link high expression of Hsp-27 to unfavourable prognosis in many cancer types such as ovarian (Geisler et al. Eur J Gynaecol Oncol, 25: 165-8, 2004), breast (Thanner et al Anticancer Res, 25: 1649-53, 2005), cervical (Ono et al Hum Pathol, 40: 41-9, 2009) and prostate cancer (abbreviated to PCa or PC) (Foster et al Br J Cancer, 101: 1137-44, 2009). The prognostic potential of Hsp-27 expression has been indicated in prostate cell lines (Morino et al In Vivo, 11: 179-84, 1997) as well as in prostate tissues where over-expression has been linked with hormone resistance and poor outcome (Foster et al Br J Cancer, 101: 1137-44, 2009, Cornford et al Cancer Res, 64: 6595-602, 2004, Rocchi et al Cancer Res, 64:6595-602, 2004). In addition, Hsp-27 contributes to cell invasion by increasing matrix metalloproteinase type 2 activity (Berney et al Br J Cancer, 100: 888-93, 2009) as well as by coordinating F-actin filament alignment, thus promoting locomotor force within a cell (Graceffa, P. Biochem Res Int, 2011: 901572, 2011).

PCa is a major public health problem, being one of the main malignancies affecting males and moreover is a biologically heterogeneous disease. However, most men do not experience significant morbidity or premature death if left untreated. For clinical management of non-metastatic disease, thus far the two most important variables are the serum level of prostate specific antigen (PSA) (Stamey et al N Engl J Med, 317: 909-16, 1987) and Gleason score (Cuzick et al Br J Cancer, 95: 1186-94, 2006).

Prognosis refers to the expected biologic aggressive potential of a patient's PCa to spread to other organs. The Gleason Score, the most widespread method of prostate cancer tissue grading used today, is the single most important prognostic factor in PCa. It is one determinant of a patient's specific risk of dying due to prostate cancer. Hence, once the diagnosis of prostate cancer is made on a biopsy, tumour grading, especially the Gleason score, is often then relied upon in considering options for therapy.

The Gleason Score is designed to ensure identify the prostate cancer's stage. This tumour scoring system is based upon microscopic tumour patterns that are measured by a pathologist, based on a prostate biopsy.

The Gleason Score may be between 2 to 10. Several markers are observed, and then, additional ones are added for a final sum. (The "Gleason Score" and the "Gleason Sum" are same). The Gleason Score is the sum of the primary Gleason grade and the secondary Gleason grades.

When PCa is present in the biopsy, the Gleason score is based upon the degree of loss of the normal glandular tissue architecture (i.e. shape, size and differentiation of the glands) as originally described and developed by Dr. Donald Gleason in 1974 (Gleason D F, and Mellinger G T, J Urol 111:58-64, 1974).

The classic Gleason scoring diagram shows five basic tissue patterns that are technically referred to as tumour "grades". The subjective microscopic determination of this loss of normal glandular structure caused by the cancer is abstractly represented by a grade, a number ranging from 1 to 5, with 5 being the worst grade possible. The biopsy Gleason score is a sum of the primary grade (representing the majority of tumour) and a secondary grade (assigned to the minority of the tumour), and is a number ranging from 2 to 10. The higher the Gleason score, the more aggressive the tumour is likely to act and the worse the patient's prognosis.

Grade 1: the cancerous tissue will closely resemble the normal tissue

Grade 2: tissue which still has well advanced structures, such as the glands; though they are also much larger and also the tissues are present amongst them.

Grade 3: tissue still has the recognizable glands; though, the cells are dimmer

Grade 4: the tissue has hardly any glands which are identifiable

Grade 5: there are no identifiable glands in the tissue

The Primary Gleason grade has to be greater than 50% of the total pattern seen (i.e. the pattern of the majority of the cancer observed). The Secondary Gleason grade has to be less than 50%, but at least 5%, of the pattern of the total cancer observed. The sum of the primary and secondary Gleason grades is shown as the Gleason score or sum (i.e. primary grade+secondary grade=GS; i.e. 4+3 or 3+4=GS 7).

Although PSA is useful for early detection, its poor specificity leads to unnecessary invasive examinations and biopsy of large numbers of healthy men, risk of over-diagnosis and over-treatment as well as increased health care burden (Schroder et al N Engl J Med, 360: 1320-8, 2009, Moore et al BJU Int, 104: 1592-8, 2009). Therefore, there is an urgent demand for new molecular markers specifically capable of separating aggressive from indolent PCa (Foster, C. S., and Cooper, C. S. Biomark Med, 3: 329-33, 2009).

During the last decade an extensive search for such biomarkers has led to a number of candidates such as PCA3 (Hessels et al Expert Rev Mol Diagn, 4: 513-26, 2004), TMPRSS-ERG (Mehra, et al. Cancer Res, 68: 3584-90, 2008), Ki-67 (Berney et al Br J Cancer, 100: 888-93, 2009) and Hsp-27 (Foster et al Br J Cancer, 101: 1137-44, 2009) but none have so far been validated for widespread use.

Early during prostate carcinogenesis, expression of Hsp-27 protein detected immunohistochemically becomes universally abrogated but may be re-expressed in subsequent invasive cancer cells. If re-expression of Hsp-27 occurs, then the malignancy usually develops an aggressive phenotype whereas cancers that remain negative are relatively indolent (Cornford et al Cancer Res, 64: 6595-602, 2004). However, the mechanisms responsible for Hsp-27 down-regulation and subsequent re-expression are presently unknown. Since aberrant DNA methylation (DNAme) is involved in cancer development and progression (Berdasco, M., and Esteller, M. Dev Cell, 19: 698-711, 2010), assessment of DNAme changes may provide novel potent diagnostic and prognostic cancer biomarkers. The majority of CG dyads in the human genome are methylated with the exception of CG rich regions, so called CpG islands. CpG islands mainly cover the promoter and first exon of over half of human genes (Cedar, H., and Bergman, Y. Nat Rev Genet, 10: 295-304, 2009) and hypermethylation is associated with repressed transcription of many tumour suppressor genes (Sakai et al Am J Hum Genet, 48: 880-8, 1991, Herman, J. G., and Baylin, S. B. N Engl J Med, 349: 2042-54, 2003). HSPB1 DNAme status in PCa has not been examined previously and considering the up-regulation of Hsp-27 in aggressive PCa such an investigation is warranted. Therefore the aims of this study were to map the methylation status of promoter, exon and intron regions of the HSPB1 gene, as well as to assess the diagnostic biomarker potential of DNAme by comparing the status in benign prostate hyperplasia (BPH) and PCa biopsies. Further we aimed to test for a possible association between Hsp-27 protein levels and methylation of HSPB1. Finally, we explored the prognostic biomarker potential of HSPB1 DNAme by analysing the association between DNAme and death as a consequence of PCa disease as well Gleason score in the Transatlantic Prostate Group (TAPG) cohort of men (Cuzick et al Br J Cancer, 95: 1186-94, 2006).

The present invention therefore provides a method for determining the prognosis of prostate cancer in a subject. The method comprises assessing the DNA methylation status of the HSPB1 gene in a prostate cancer sample. The method may find particular use in determining the prognosis for subjects who have a Gleason Score equal to or below 7, but is equally useful for subjects with no known Gleason Score. The HSPB1 gene (NCBI NT_007933.5; version NC_000007.13 GI: 224589819) is located on human chromosome 7 and is composed of three exons and two introns spanning 1461 base pairs.

The analysis of the DNA methylation status may comprise analysing the methylation status of a genomic region of HSPB1. Analysis of the DNA methylation status of a genomic region of HSPB1 means analysing the methylation status of at least one CpG position per genomic region of HSPB1.

The methylation status may be analyzed by non-methylation-specific polymerase chain reaction (PCR) based methods, methylation-based methods, sequencing based methods including "Next Generation Sequencing" (for example, nanopore sequencing where the nucleotide methyl-cytosine is detected directly due to its size and charge characteristics as it passes through a pore), or microarray-based methods.

The present invention therefore provides a method for determining the prognosis of prostate cancer in a subject, comprising assessing the DNA methylation status of the HSPB1 gene in a prostate cancer sample. The sample may suitably be from a subject who has a Gleason Score equal to or below 7. In such methods, the analysis of the DNA methylation status can comprise analysing the methylation status of a genomic region of HSPB1. The analysis of the methylation status of a genomic region of HSPB1 can comprise analysis of the methylation status of at least one CpG position per genomic region of HSPB1. The methylation status can be analysed by non-methylation-specific PCR based methods, methylation-based methods, microarray-based methods or nanopore sequencing methods. The non-methylation-specific PCR based method may be pyrosequencing. In an alternative embodiment, the method may further comprise assessing the DNA methylation status of at least one of the DPYS gene and the CCND2 gene.

The present invention also provides a nucleic acid molecule that hybridizes under stringent conditions in the vicinity of one of the genomic regions according to SEQ ID NO. 7, wherein said vicinity is any position having a distance of up to 1000 nucleotides from the 3'- or 5'-end of said genomic region and wherein said vicinity includes the genomic region itself. The nucleic acid sequence may also be used in a kit for use in determining the prognosis of prostate cancer as described herein.

As described herein, the invention provides a kit comprising a plurality of nucleic acid sequences as defined above. In said kits, the kit may further comprise one or more nucleic acid sequences that hybridize under stringent conditions to at least one of the DPYS gene and the CCND2 gene.

The invention also provides a method for determining the prognosis of prostate cancer, comprising the steps of analysing in a sample of a subject the DNA methylation status of HSPB1 according to SEQ ID NO. 7, wherein, if HSPB1 shows a median methylation value of less than 20% the sample is categorized as a sample from a patient with prostate cancer with a good prognosis.

In the methods of the invention, the prognosis of prostate cancer may be determined in combination with one or more of (i) an analysis of the methylation status of one or more other genes, (ii) an analysis of one or more other DNA biomarkers, or (iii) an analysis of the amount or concentration or activity of a protein or set of proteins or of the expression of an RNA or set of RNAs. In some embodiments, (i) comprises the analysis of the methylation status of one or more genes selected from the group consisting of CCND2, DPYS, SFN, SERPINB5, TWIST1 and SLIT2. In one particular embodiment, (i) comprises the analysis of the methylation status of the genes CCND2 and DPYS. Further, (ii) may comprise the analysis of gene expression of one or more DNA biomarkers selected from the group consisting of PCA3, Ki67, TMPRSS-ERG, GSTP1, multi-drug resistance protein 1 (MDR1), O-6-methylguanine-DNA methyltransferase (MGMT), Ras association domain family member 1 (RASSF1), retinoic acid receptor beta (RARB), adenomatous polyposis coli (APC), androgen receptor (AR), cyclin-dependent kinase inhibitor 2A (CDKN2A), E-cadherin (CDH1) and/or CD44.

In any method of the invention, (iii) may comprise an analysis of the amount of PSA present in a sample. The step of analysis of PSA in a sample may therefore be part of any method of the invention.

The gene DPSY (NC_000008.10) is located on human chromosome 8, and is 87626 base pairs (version NC_000008.10 GI:224589820; synonyms DHP; DHPase, dihydropyrimidinase), see Nature 439 (7074), 331-335 (2006), Nature 431 (7011), 931-945 (2004) and Nature 409 (6822), 860-921 (2001).

The gene CCND2 (NC_000012.11) is located on human chromosome 12, and is 31621 base pairs (version NC_000012.11 GI:224589803; synonyms cyclin D2, KIAK0002), see Nature 440 (7082), 346-351 (2006), Nature 431 (7011), 931-945 (2004) and Nature 409 (6822), 860-921 (2001).

Any suitable quantitative DNA methylation assay can therefore be used in connection with the present invention. Non-methylation-specific PCR based method can include pyrosequencing.

The term "amplified", when applied to a nucleic acid sequence, refers to a process whereby one or more copies of a particular nucleic acid sequence is generated from a nucleic acid template sequence, preferably by the method of polymerase chain reaction. The reaction mix comprises dNTPs (each of the four deoxynucleotides dATP, dCTP, dGTP, and dTTP), primers, buffers, DNA polymerase, and nucleic acid template. The PCR reaction can comprise (a) providing a "primer pair" wherein a first primer contains a sequence complementary to the sense strand of the target nucleic acid sequence and primes the synthesis of a complementary second DNA strand, and a second primer contains a sequence complementary to the antisense strand of the target nucleic acid sequence and primes the synthesis of a complementary DNA strand of the antisense strand, and (b) amplifying the nucleic acid template sequence employing a nucleic acid polymerase. Usually, a Taq polymerase is used to amplify a nucleic acid template in PCR reaction. Other methods of amplification include, but are not limited to, ligase chain reaction (LCR), polynucleotide-specific based amplification, or any other method known in the art.

A "DNA biomarker" may describe (a) a genomic region that is differentially methylated, or (b) a gene that is differentially expressed, or (c) a mutation of a DNA sequence or single-nucleotide polymorphism (SNP) that can be associated with subjects having cancer or a stage of cancer compared with those not having cancer.

Any single CpG position within the area of the gene defined by assays 1 to 6 may be considered to be a suitable target for use according to the present invention. Consequently, any CpG sequence inside the designated area can be used as possible target in a diagnostic test according to the present invention.

The term "CpG position" as used herein refers to regions of DNA where a cytosine nucleotide is located at the 5' adjacent position to a guanine nucleotide in the linear sequence of bases along its length. "CpG" is shorthand for "C-phosphate-G", that is, cytosine and guanine separated by a phosphate, which links the two nucleosides together in DNA. Cytosines in CpG dinucleotides can be methylated to form 5-methylcytosine.

The invention also provides a nucleic acid molecule that hybridizes under stringent conditions in the vicinity of one of the genomic regions according to SEQ ID NO. 7, wherein said vicinity is any position having a distance of up to 1000 nucleotides from the 3'- or 5'-end of said genomic region and wherein said vicinity includes the genomic region itself. Suitably, the assay can be performed within nucleotides −500 to +2500, where the region of +750 to +1750 may be convenient in certain embodiments. Such nucleic acid sequences may therefore be used in methods or kits of the invention.

Figure 1B:
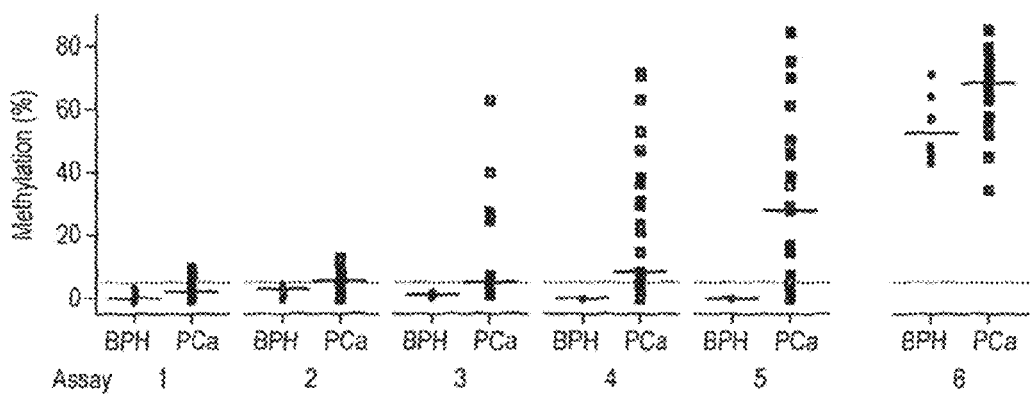

Any generally convenient region of the HSPB1 gene may be a suitable target for a nucleic acid of the invention as defined herein but some regions may be preferred. The regions (also called assays) are indicated where there are discernible differences in methylation as shown in FIGS. 1A and 1B. The boundaries of possible target sequences in the HSPB1 gene are defined by the outer sets of primers (1 and 6) that give differences between prostate cancer and non-cancer.

A nucleic acid according to the invention may suitably be 15 to 200 nucleotides in length, suitably selected from the group consisting of SEQ ID NO:1 to SEQ ID NO: 6. The nucleotides may be less than 180, 160, 140, or 120 nucleotides in length in some embodiments, with the range of 60 to 120 nucleotides or 40 to 180 nucleotides being generally convenient.

Such nucleic acids may be used as primers which may be specific for one of the genomic regions of SEQ ID NO:7. Alternatively, the nucleic acid may be a probe which may be labelled.

Suitably, the nucleic acid sequences hybridize under stringent conditions in the vicinity of one of the genomic regions after a bisulphite treatment of the genomic region.

Other nucleic acid sequences suitable for use as primers with respect to the genes DPYS and/or CCND2 are shown in Table 7 as SEQ ID NO: 8 to SEQ ID NO: 17.

The present invention also therefore provides the use of the nucleic acid sequences as defined above for the prognosis of prostate cancer.

The present invention also provides a composition for the diagnosis of cancer comprising a nucleic acid as defined above.

The present invention also therefore extends to a kit for the diagnosis of cancer comprising a nucleic acid as defined above.

The invention also provides a method for prognosis of prostate cancer, comprising the steps of analysing in a sample of a subject the DNA methylation status of HSPB1 according to SEQ ID NO. 7, wherein, if HSPB1 shows a methylation median value of above 20% the sample is categorized as a sample from a patient with prostate cancer with a poor prognosis.

Below 20%, subjects who also have a Gleason score of 7 or less have a low risk of death from prostate cancer. In subjects with a Gleason score of 7 or less with HSPB1 DNA methylation at or above 20% there is a high chance of dying of prostate cancer. Subjects with a Gleason score of 7 or less and DNA methylation above 50% are at very high risk of dying of prostate cancer.

At a 5% methylation cut-off, HSPB1 methylation has 100% specificity and 50% diagnostic sensitivity for any PCa including those of low risk. The present invention therefore provides methods which are specific and sensitive.

Methods in accordance with the present invention may also be used in conjunction with other tests such as serum levels of Prostate Specific Antigen (PSA) and the Gleason Score in order to provide information on the prognosis for any given subject.

Methods of the invention, therefore, also include methods of assessing the DNA methylation status of the HSPB1 gene in a sample, optionally including assessing the methylation status of one or more other genes, and/or analysing the gene expression of one or more biomarkers, and/or analysing the amount or concentration or activity of a protein or a set of proteins or of the expression of an RNA or a set of RNAs.

For example, such methods may include assessing the DNA methylation status of the HSPB1 gene in a sample, assessing the DNA methylation status of the DPYS gene and/or the CCND2 gene, optionally also analysing the amount of PSA present in the sample.

A "prognosis" is a prediction of the probable course and outcome of a clinical condition or disease. A prognosis of a patient is usually made by evaluating factors, markers, and/or symptoms of a disease that are indicative of a favourable or unfavourable course or outcome of the disease.

A poor prognosis is characterised as a being the increased risk for a subject of developing an aggressive cancer which, if left untreated, would lead to early death over a 5 to 9 year period. A poor prognosis therefore means an increased risk of death as compared to subjects who have a low percentage of DNA methylation of the HSBP1 marker. A good prognosis is therefore an assessment that a subject will respond well to therapy with a good chance of medium- to long-term survival over a 5 to 9 or longer year period.

The data presented in the present application indicates that a period of 7 years may be a preferred time point where the different prognosis profiles begin to become evident, but population variations suggest that a range of 5 to 9 years may also be generally useful.

The phrase "determining the prognosis" refers to the process by which the course or outcome of a condition in a patient can be predicted. The term "prognosis" does not refer to the ability to predict the course or outcome of a condition with 100% accuracy. Instead, the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively, prognosis may be expressed as the number of years on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

The present invention uses an approach based on a determination of the "differential methylation" of regions within the HSPB1 gene. The phrase "differential methylation" therefore refers to a difference in the level of DNA/cytosine methylation in a prostate cancer positive sample from a subject with a poor prognosis as compared with the level of DNA methylation in a sample from a subject with a good prognosis.

Differential methylation and specific levels or patterns of DNA methylation can be used as prognostic and predictive biomarkers once the correct cut-off or predictive characteristics have been defined. The "DNA methylation status" is interchangeable with the term "DNA methylation level" and may be assessed by determining the ratio of methylated and non-methylated DNA for a genomic region or a portion thereof and is quoted in percentage. The methylation status is classified herein as either increased or decreased and may relate to a person with recurrence of cancer as compared to a control person who did experience a recurrence during a similar observation period.

A "cut-off value" is defined as follows: a specific DNA methylation level above which results are regarded as positive (or negative for a gene with a reverse association) versus when the methylation level is below the cut-off the results are regarded as negative (or positive for a gene with reverse association). To account for biological variability that is known to be typical of all living biological systems such as humans or other organisms it is reasonable to consider ranges of values and thus all cut-off values herein may vary by plus minus 15%, plus minus 10% or preferably only plus minus 5%. This also depends on the experimental set-up.

DNA methylation status may be analysed using any generally suitable approach. The phrase "analysing the methylation status" relates to the means and methods useful for assessing the methylation status. Useful methods are bisulphite-based methods, such as bisulphite-based mass spectrometry or bisulphite-based sequencing methods.

Such methods of "bisulphite sequencing" comprise the steps of (a) treating the DNA of interest with bisulphite, thereby converting non-methylated cytosines to uracils and leaving methylated cytosines unaffected and (b) sequencing the treated DNA, wherein the existence of a methylated cytosine is revealed by the detection of a non-converted cytosine and the absence of a methylated cytosine is revealed by the detection of an uracil.

The phrase "genomic region specific primers" as used herein refers to a primer pair complementary to a sequence in the vicinity of a genomic region according to the invention, which can be produced by methods of amplification of double-stranded DNA complementary to a genomic region of the invention.

The term "genomic region specific probe" as used herein refers to a probe that selectively hybridizes to a DNA product of a genomic region. In one embodiment a genomic region specific probe can be a probe labelled, for example, with a fluorophore and a quencher, such as a TaqMan® probe or a Molecular Beacon probe.

As used herein, the terms "hybridizing to" and "hybridization" are interchangeably used with the term "specific for" and refer to the sequence-specific non-covalent binding interactions with a complementary nucleic acid, for example, interactions between a target nucleic acid sequence and a target specific nucleic acid primer or probe. In a preferred embodiment a nucleic acid, which hybridizes, is one which hybridizes with a selectivity of greater than 70%, greater than 80%, greater than 90% and most preferably of 100% (i.e. cross hybridization with other DNA species preferably occurs at less than 30%, less than 20%, less than 10%). As would be understood to a person skilled in the art, a nucleic acid, which "hybridizes" to the DNA product of a genomic region of the invention, can be determined taking into account the length and composition.

As used herein, "isolated" when used in reference to a nucleic acid means that a naturally occurring sequence has been removed from its normal cellular (e.g. chromosomal) environment or is synthesised in a non-natural environment (e.g. artificially synthesised). Thus, an "isolated" sequence may be in a cell-free solution or placed in a different cellular environment.

As used herein, a "kit" is a packaged combination optionally including instructions for use of the combination and/or other reactions and components for such use.

As used herein, "nucleic acid(s)" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid(s)" also includes DNA as described above that contain one or more modified bases. Thus, DNA with backbones modified for stability or for other reasons are "nucleic acids". The term "nucleic acid(s)" as it is used herein embraces such chemically, enzymatically or metabolically modified forms of nucleic acids, as well as the chemical forms of DNA characteristic of viruses and cells, including for example, simple and complex cells.

The term "primer" as used herein refers to a nucleic acid, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e. in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the nucleic acid primer typically contains 15-25 or more nucleotides, although it may contain fewer nucleotides.

As used herein, the term "probe" means nucleic acid and analogs thereof and refers to a range of chemical species that recognise polynucleotide target sequences through hydrogen bonding interactions with the nucleotide bases of the target sequences. The probe or the target sequences may be single- or double-stranded DNA. A probe is at least 8 nucleotides in length and less than the length of a complete polynucleotide target sequence. A probe may be 10, 20, 30, 50, 75, 100, 150, 200, 250, 400, 500 and up to 10,000 nucleotides in length. Probes can include nucleic acids modified so as to have one or more tags which are detectable by fluorescence, chemiluminescence and the like ("labelled probe"). The labelled probe can also be modified so as to have both one or more detectable tags and one or more quencher molecules, for example Taqman® and Molecular Beacon® probes. The nucleic acid and analogs thereof may be DNA, or analogs of DNA, commonly referred to as antisense oligomers or antisense nucleic acid. Such DNA analogs comprise but are not limited to 2-'O-alkyl sugar modifications, methylphosphonate, phosphorothiate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)-Oligonucleotide Analogues with an Achiral Peptide Backbone, (1992)).

The term "sample" is used herein to refer to tissue per se, cancer tissue, potential cancer tissue, prostate tissue, blood, urine, semen, prostatic secretions, needle aspirations or isolated prostate cells, cells originating from a subject, preferably from prostate tissue, prostatic secretions, or isolated prostate cells, most preferably to prostate tissue.

As used herein, "stringent conditions for hybridization" are known to those skilled in the art and can be found in Current Protocols in Molecular Biology, John Wiley & Sons, N.Y., 6.3.1-6.3.6, 1991. Stringent conditions are defined as equivalent to hybridization in 6× sodium chloride/sodium citrate (SSC) at 45° C., followed by a wash in 0.2×SSC, 0.1% SDS at 65° C.

As used herein, the terms "subject" and "patient" are used interchangeably to refer to a human or a non-human mammal. The subject may be a companion non-human mammal (i.e. a pet, such as a dog, a cat, a guinea pig, or a non-human primate, such as a monkey or a chimpanzee), an agricultural farm animal mammal, e.g. an ungulate mammal (such as a horse, a cow, a pig, or a goat) or a laboratory non-human mammal (e.g., a mouse and a rat). The invention may find greatest application in connection with the treatment of male human subjects.

As used herein, the term "in the vicinity of a genomic region" refers to a position outside or within said genomic region. As would be understood by a person skilled in the art the position may have a distance up to 1000 nucleotides (nt), preferably up to 500 nucleotides, more preferably up to 200 nucleotides from the 5' or 3' end of the genomic region. Even more preferably the position is located at the 5' or 3' end of said genomic region. In another embodiment of the invention the position is within said genomic region.

The prognosis of prostate cancer in a subject according to the methods of the present invention may also be determined in combination with one or more of (i) an analysis of the methylation status of another gene, (ii) an analysis of another DNA biomarker, or (iii) an analysis of the amount or concentration or activity of a protein.

The analysis of the methylation status of one or more genes can include one or more genes selected from the group consisting of CCND2, SFN, SERPINB5, TWIST1, and SLIT2. The analysis of gene expression can include of one or more DNA biomarkers selected from the group consisting of PCA3, Ki67, TMPRSS-ERG, GSTP1, multi-drug resistance protein 1 (MDR1), O-6-methylguanine-DNA methyltransferase (MGMT), Ras association domain family member 1 (RASSF1), retinoic acid receptor beta (RARB), adenomatous polyposis coli (APC), androgen receptor (AR), cyclin-dependent kinase inhibitor 2A (CDKN2A), E-cadherin (CDH1) and/or CD44. The analysis of the amount or concentration or activity of a protein in a sample may comprise an analysis of the amount of PSA present in a sample.

Preferred features for the second and subsequent aspects of the invention are as for the first aspect of the invention mutatis mutandis.

The present invention will now be described by way of reference to the following Examples and accompanying Drawings which are present for the purposes of illustration only and are not to be construed as being limiting on the invention.

Table 1 shows clinical and pathological characteristics of the 367 FFPE tumours, with univariate Cox model's hazard ratio with 95% confidence interval and the p-value of the likelihood ratio test. Notes: [a] Differences in totals are due to missing values, [b] Continuous methylation per 10 percent change.

Table 2 shows primers used for amplification of different CpG regions in HSPB1 gene. Notes: [a] base pairs, [b] The position of 0 is start of the exon 1, [c] Biotin Table 3 shows Analysis of variance tables for the fitted Cox model[a]. Notes: [a] The ANOVA output showing the contribution importance of predictors in the Cox multivariate model for the modified HSPB1 DNAme, the categorized age, Gleason score, PSA level and the interaction between Gleason score*HSPB1 DNAme versus the primary event of interest DPCa as judged by partial Wald $\chi^2$. Interaction effects by themselves have been removed as has the Gleason effect. The predictors in the fitted Cox model were selected as an adequacy of subset of predictors of interest. [b] Factor+Higher Order Factors Table 4 shows univariate Cox regression of 13 genes and available clinical variables. Notes: The hazard rations were calculated per 10 units increase in age, PSA, extent of disease and gene methylation while it is per each unit increase in Gleason score, i.e 4 through 10, [b] LR=likelihood ratio test, [c] Adjusted for false discovery rate, [d] The total number of patients for which DNAme was successfully measured. The clinical variables were available for all men included in the study, [e] The number of patients for which a DNA methylation result was obtained and who died of prostate cancer.

Table 5 shows multivariate Cox models with hazard ratio, $\chi^2$ and P-value in each model. Efficiency of the different models is compared by the likelihood ratio test. Notes: [a] Cross-product of Gleason score multiplied by HSPB1 methylation. For construction of a full model, all clinical variables and genes were included as well as interaction terms between each of the genes and the variables. The only significant interaction was found for Gleason score and HSPB1. [b] Variable not included in model.

Figure 10:
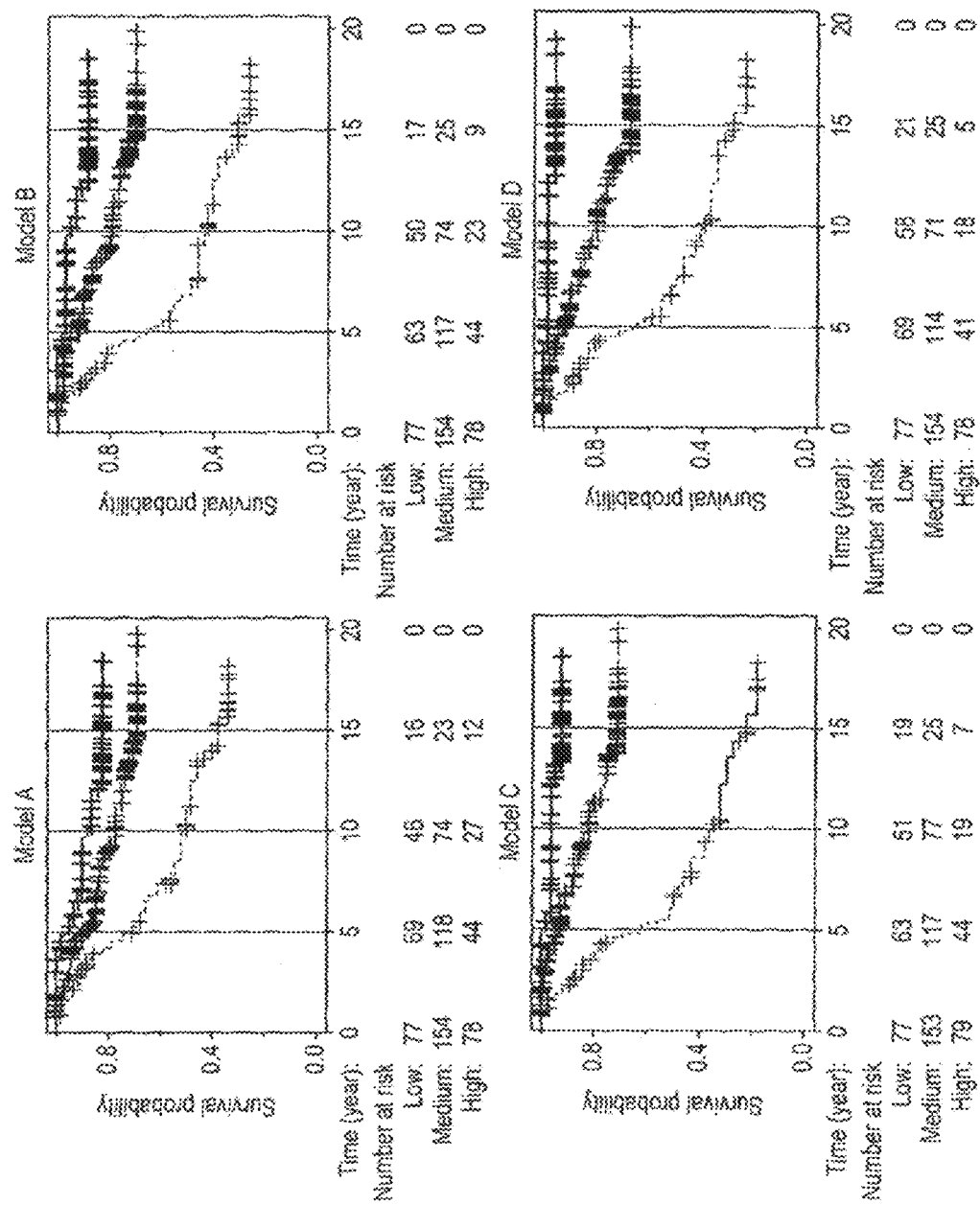

Table 6 shows Proportion of death in the groups low, medium and high as shown in FIG. 10 and prediction value of different models. Notes: [a] All models have P-value<0.0001, [b] Model including Gleason score, PSA, HSPB1× Gleason score interaction term and methylation of DPYS, HSPB1, and CCND2.

Table 7 shows primers for CCND2 and DPYS genes.

FIGS. 1A and 1B. CpG islands and associated methylation levels in the HSPB1 gene. A) Methprimer identified 5 CpG islands (shaded), the first in the promoter region (black solid line), a second covering exon1 (striped box), a third and fourth within intron1 (dotted line) and a fifth in exon2. B) Median of methylation measurement in fresh frozen 10 BPH (circle) and 27 PCa (square) show the increasing separation between BPH and PCa going in 3' direction, differences between BPH and PCa were all significant by the Wilcoxon test with the maximum difference (p<0.0001) provided by assay 5. The dashed line indicates 5% methylation.

Figure 2A:
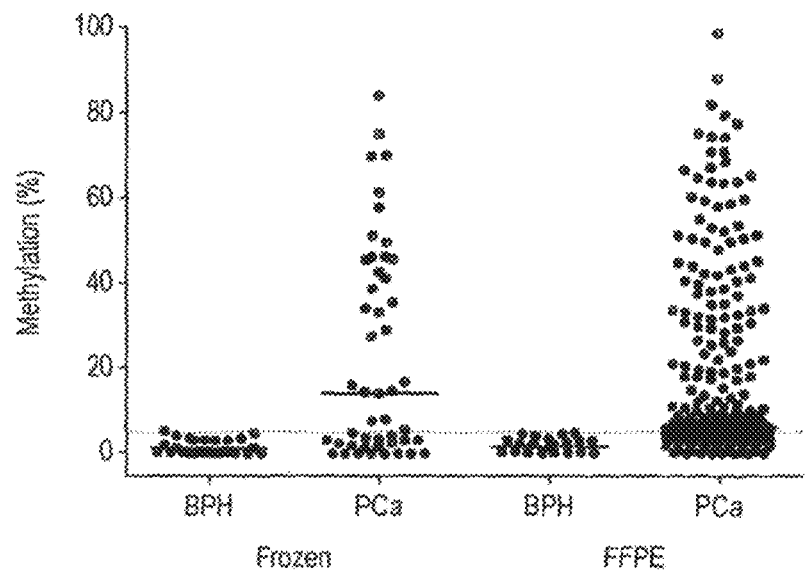
Figure 2B:
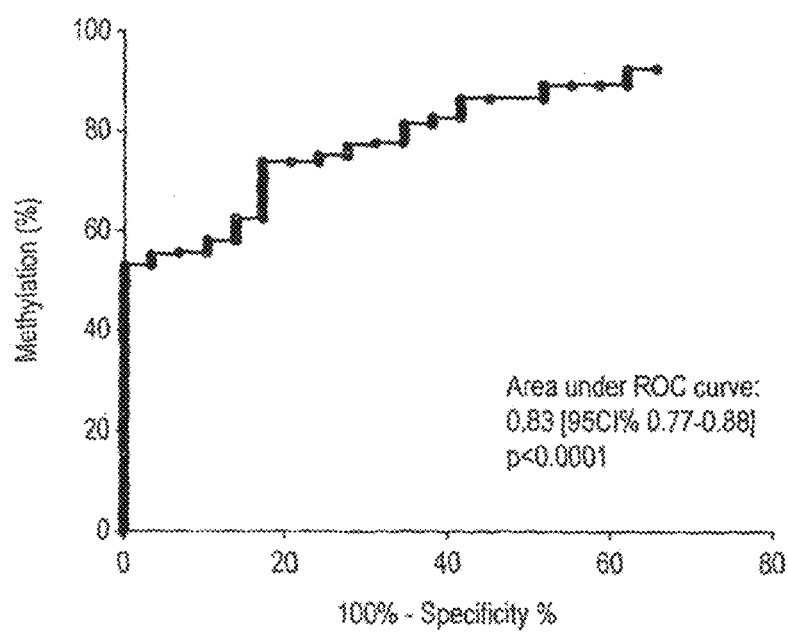

FIGS. 2A and 2B. A) The unmodified methylation of HPSB1 in 29 fresh frozen BPH and 48 PCa tissues compared to 29 FFPE BPH and 349 PCa. The dotted line shows 5% methylation B) In order to visualize the diagnostic efficacy of HPSB1 methylation measured in the FPPE tissues in absence of an arbitrary cut-off value, the data were summarized using a Receiver Operating Characteristic curve (ROC). Based on the sensitivity and specificity, highest possible specificity (100%) was obtained at cut off 5%, with corresponding sensitivity 50%.

Figure 3:
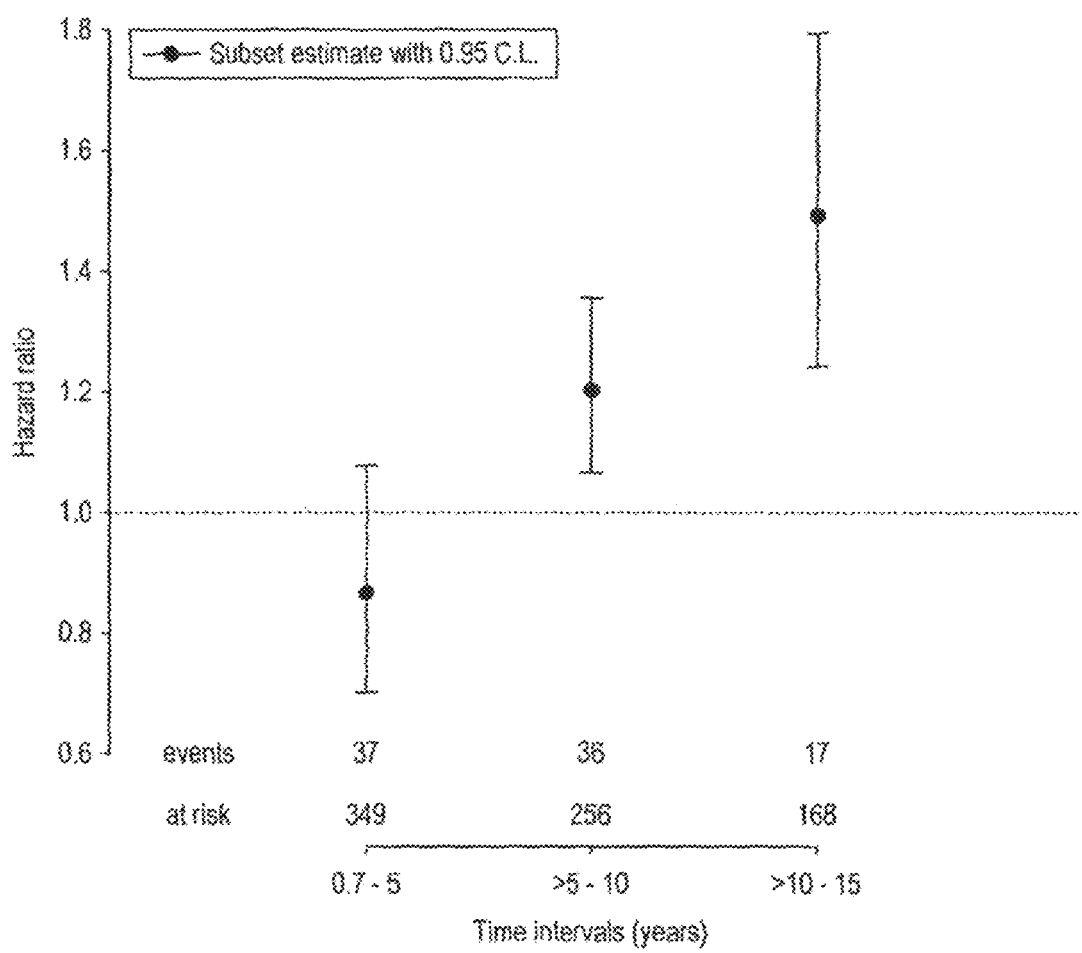

FIG. 3. Stratified hazard ratio with 95% confidence intervals associated with ten unit increase of the HSPB1 continuous gene values over time. In 349 patients with prostate cancer 91 suffered prostate cancer death. Time was stratified into intervals of five years, and within each interval a Cox model was fitted. The hazard ration in each interval can be interpreted as follows: For every 10% increase in the DNA methylation of the HSPB1 gene, the hazard rate changes by a factor of 0.87, 1.20 and 1.50 at three years, seven years and 13 years, respectively. The HSPB1 methylation is seen to have a strong effect only after 7 years.

Figure 4A:
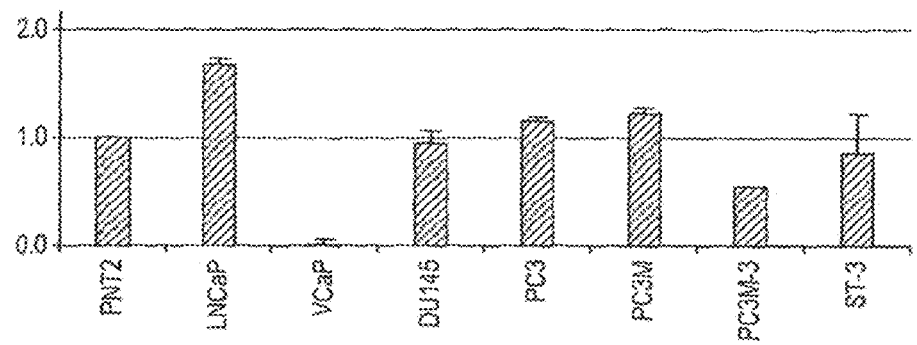
Figure 4B:
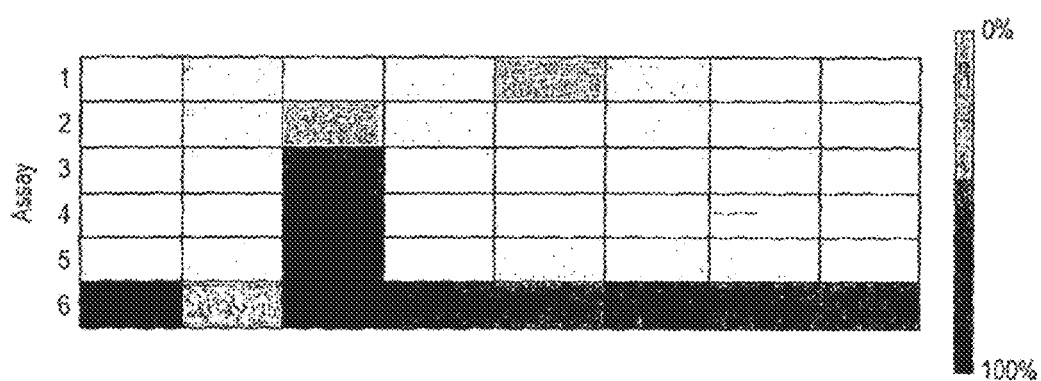
Figure 6A:
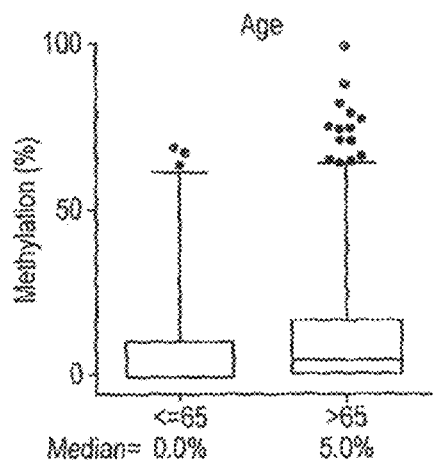
Figure 6B:
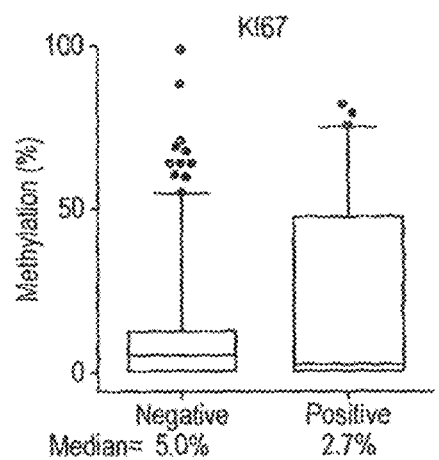
Figure 6C:
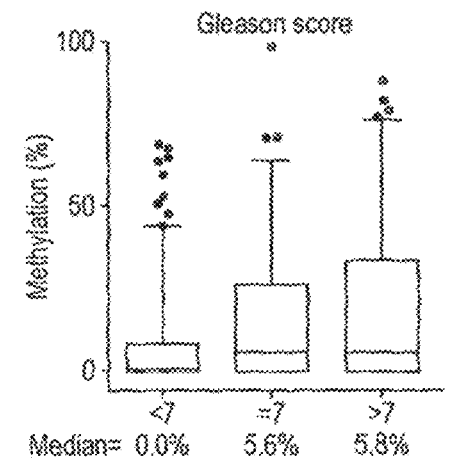
Figure 6D:
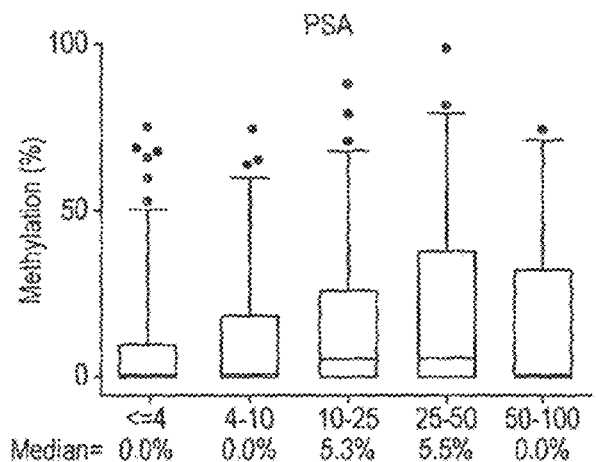
Figure 6E:
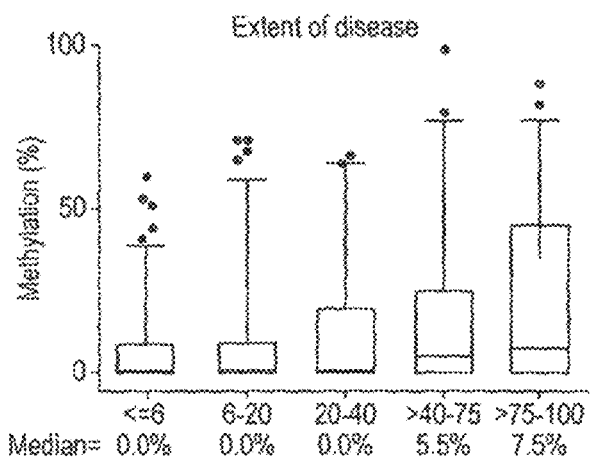
Figure 6F:
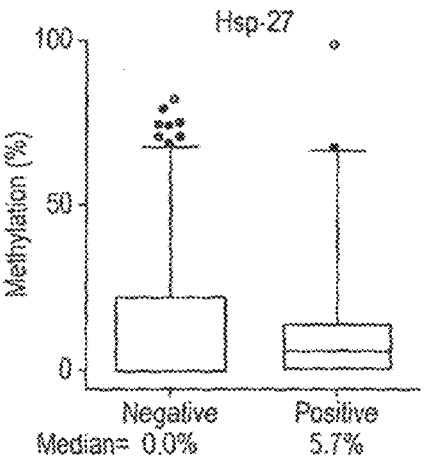

FIGS. 4A and 4B. Hsp-27 expression and gene methylation in eight investigated cell lines. A) Mean Hsp-27 generic expression (fold-difference) relative to the immortalized prostate epithelial cell line PNT2+/−1 SD was measured by Western blot. B) The methylation of six investigated regions in corresponding cell lines are shown in grayscale.

FIG. 5. HSPB1 sequence taken from UCSC Genome Browser website including 500 bp upstream sequence from the first exon.

FIGS. 6A, 6B, 6C, 6D, 6E, and 6F. Association between DNA methylation in PCa and a) age b) KI67 c) Gleason Score d) PSA e) extent of disease and f) Hsp-27 IHC staining. Whiskers of the boxplot mark the 5th and 95th percentiles, the box 25th percentile, median and 75 percentile, while extreme values are shown by (•). Cuzick test for trend showed significant association between DNAme and extent of disease (p<0.0001) and Gleason score (p=0.005) but not PSA (p=0.07). Wilcoxon test showed no association between DNAme and age (p=0.2), Hsp-27 staining (p=0.6) or KI67 score (p=0.2)

Figure 7:
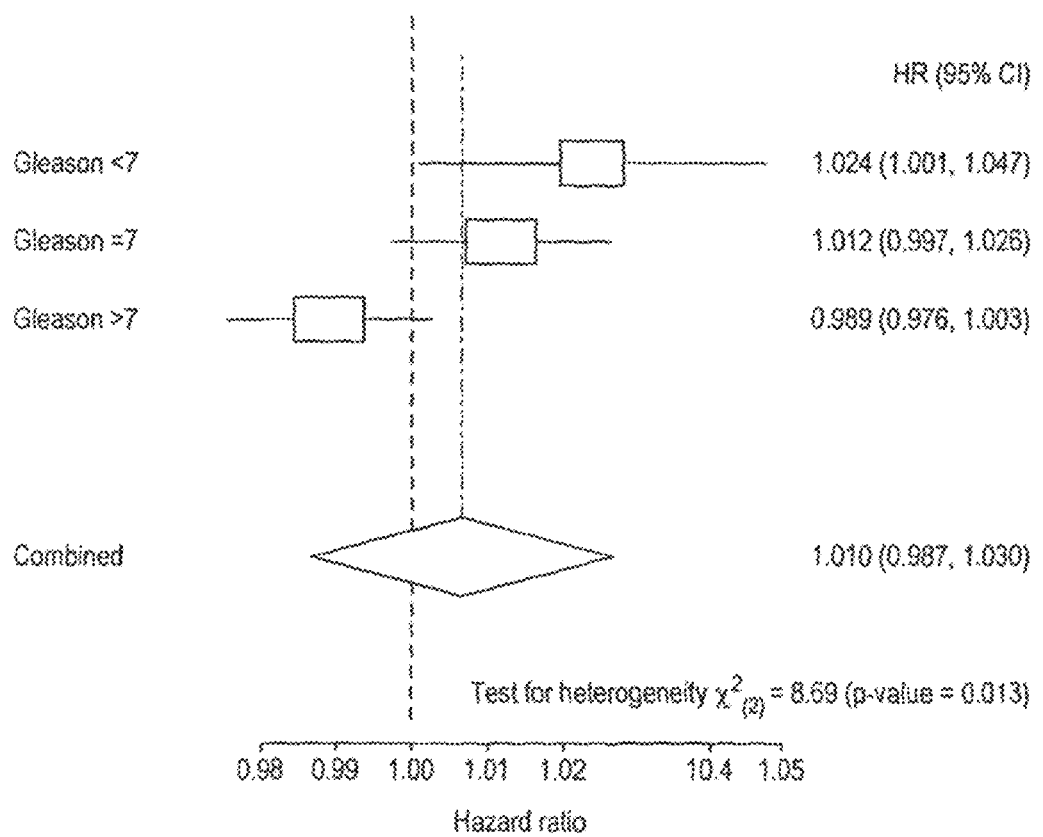

FIG. 7. Forest plots indicating the effect of hazard ratios of HSPB1 DNAme on prostate cancer survival in a Cox multivariate model by Gleason subgroups. The graph shows for each subgroup the hazard ratio for a 1% step in HSPB DNAme with the 95% confidence interval (represented by a horizontal line) and the point estimate is represented by a square, where the size of the square corresponds to the weight of the group in this meta-analysis. The vertical dashed-dotted lines provide a visual comparison of the pooled hazard ratio with the corresponding group hazard ratios. The dashed vertical line is at the null value (HR=1.0).

Figure 8:
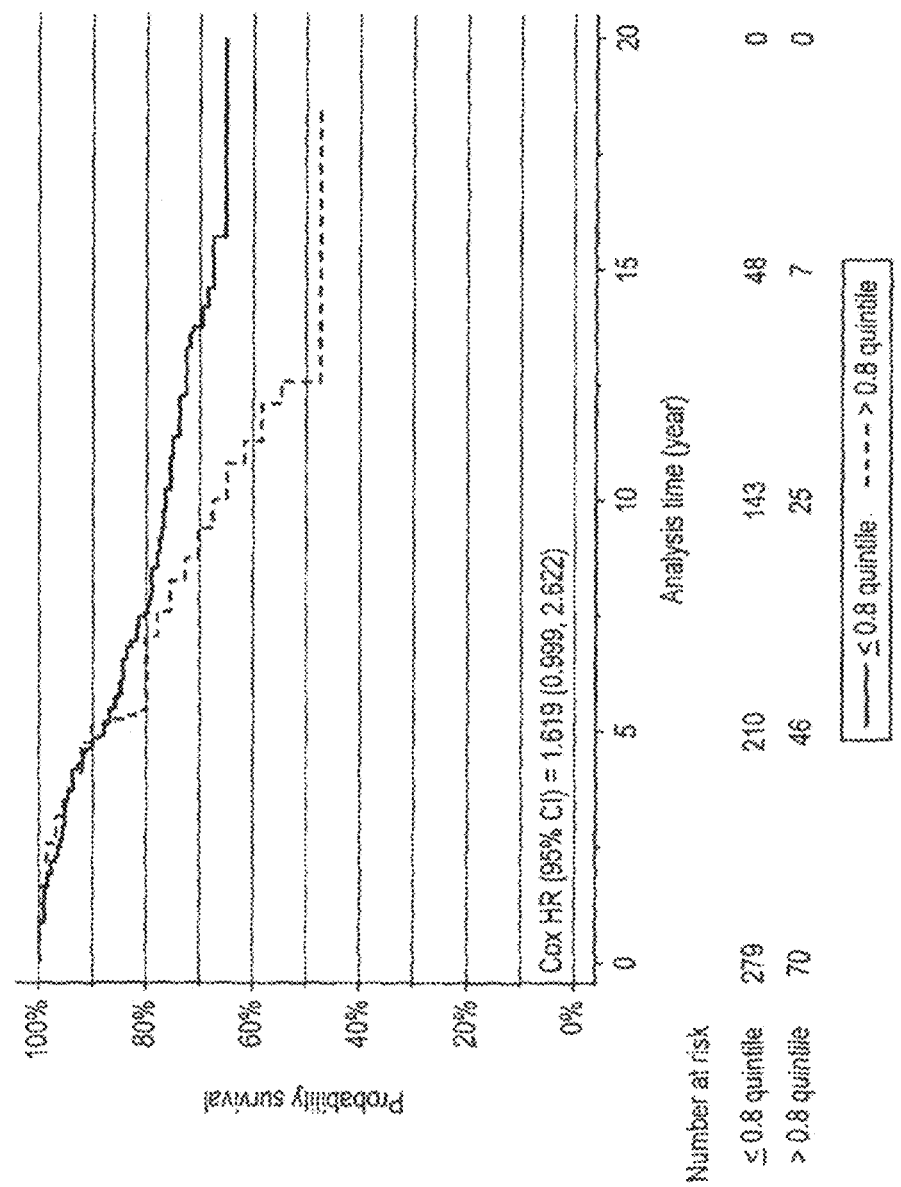

FIG. 8. Kaplan-Meier curve comparing survival in patients with two groups where HSPB1 DNAme was either above or below 24%. The DNAme level of 24% is the 0.8 quintile value and was obtained by fitting a Cox model with the dichotomized HSPB1 DNAme versus the primary event of interest died of PCa. This has been done for each cut-off value of the 0.4, 0.6 and 0.8 quintile values and 0.8 quintile was selected according to the smallest p-value of the likelihood ratio test (p-value=0.06). The hazard ratio with 95% CI of 10% DNAme change after 7.1 years was 1.20 (1.07, 1.36) (FIG. 3).

Figure 9:
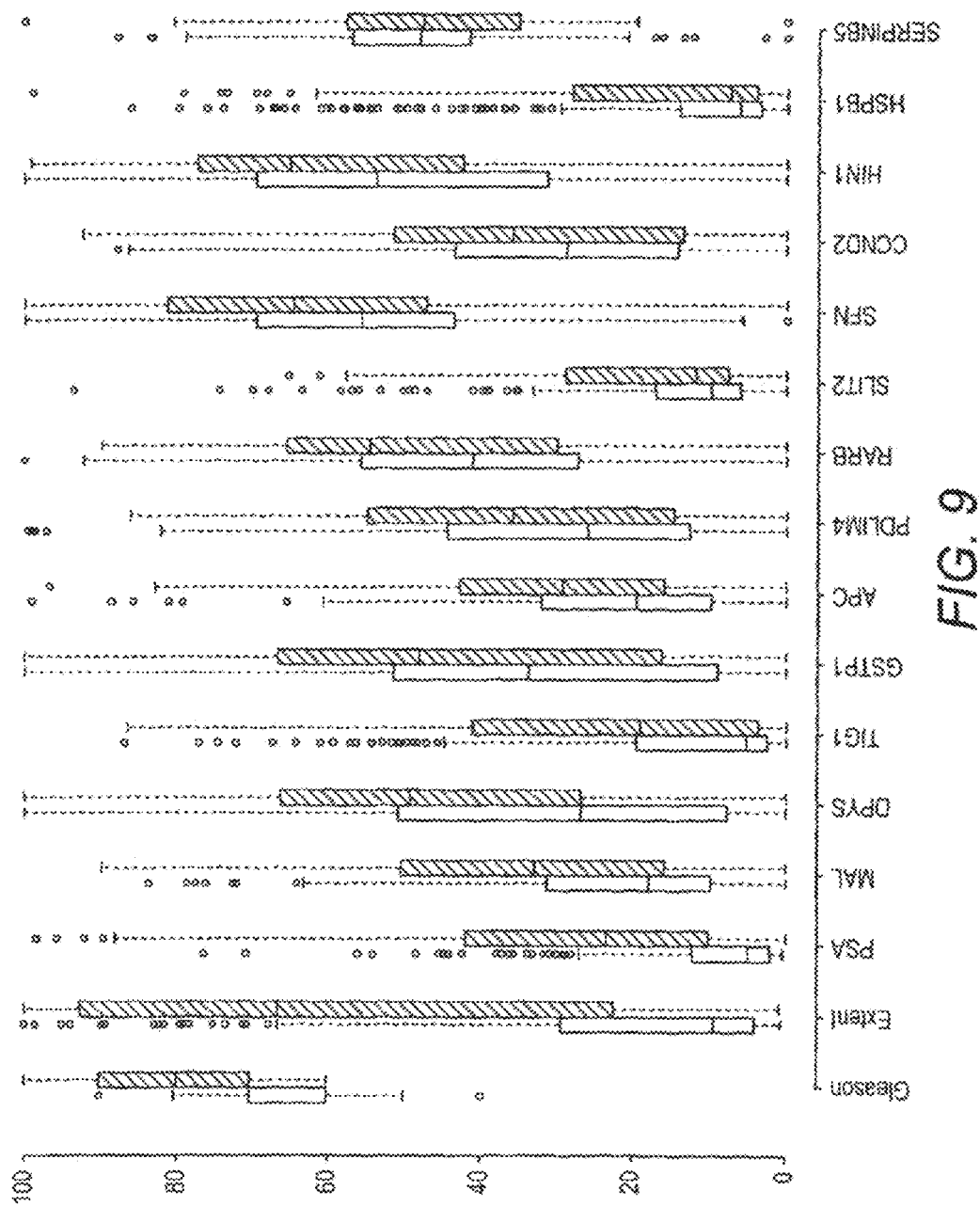

FIG. 9. Comparison and distribution of DNA methylation percent (y-axis) in each of the investigated genes to the clinical variables in men who died of prostate cancer (grey box) compared to the censored men who were alive at the last visit or died of other causes (white box). Whiskers of the boxplot mark the 5th and 95th percentiles, the box 25th percentile, median and 75 percentile, while extreme values are shown by (•). For graphical presentation, all Gleason score values were scaled by a factor of 10.

FIG. 10. Kaplan Meier survival analysis curves for the fitted models A) DPYS, GSTP1 and MAL, B) PSA and DNAme of DPYS, HSPB1, MAL and TIG1, C) Gleason score and PSA and D) the full model with Gleason score, PSA, DPYS, HSPB1, HSPB1× Gleason score and CCND2. Low (black solid line), medium (gray dashed line) and high risk group (blue dashed line) were separated by the 25% and 75% quantiles.

Figure 11:
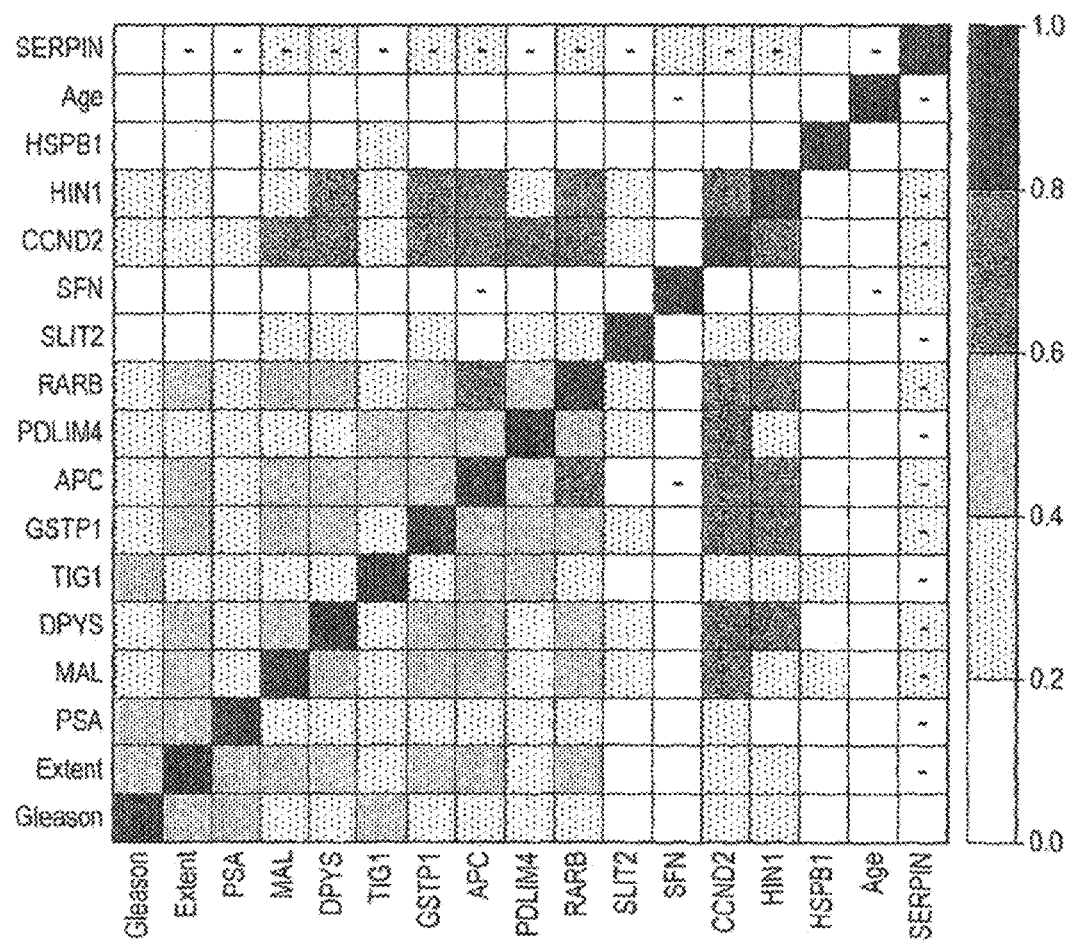

FIG. 11. Heatmap of Spearman correlation of methylation between each pair of genes and clinical variables. The shade depends on the absolute correlation; negative correlations are marked with (−) in the cell.

Figure 12A:
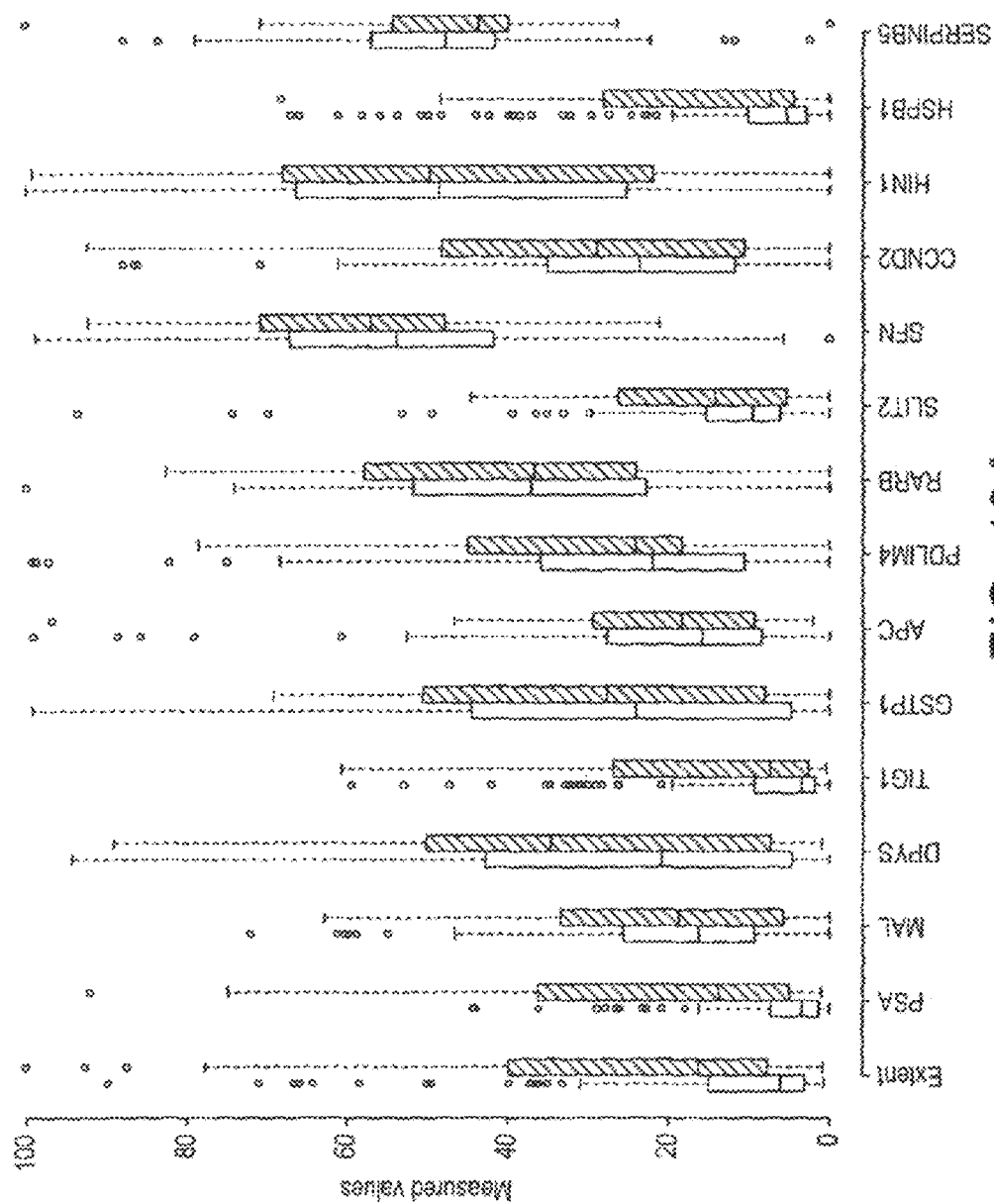
Figure 12B:
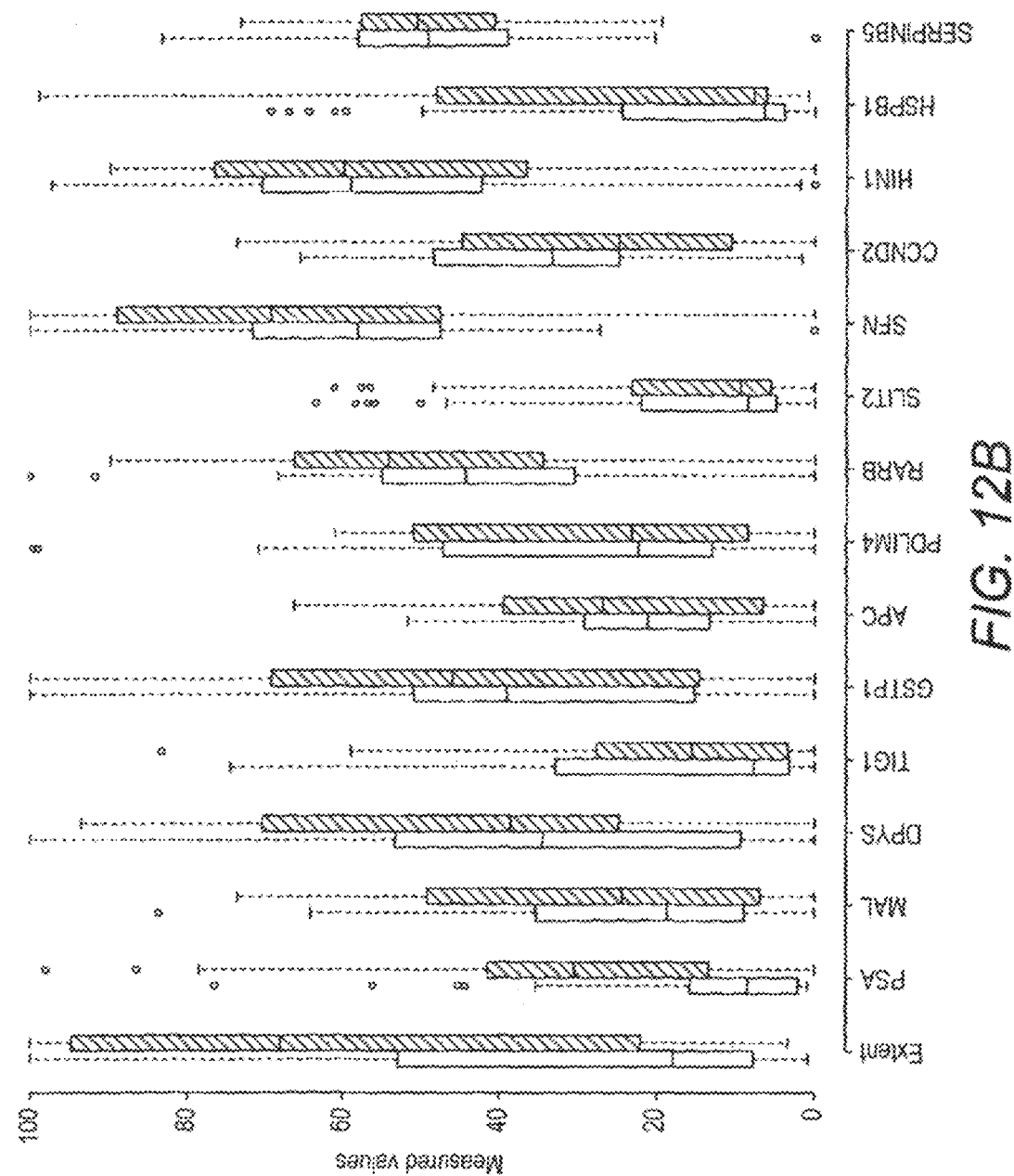
Figure 12C:
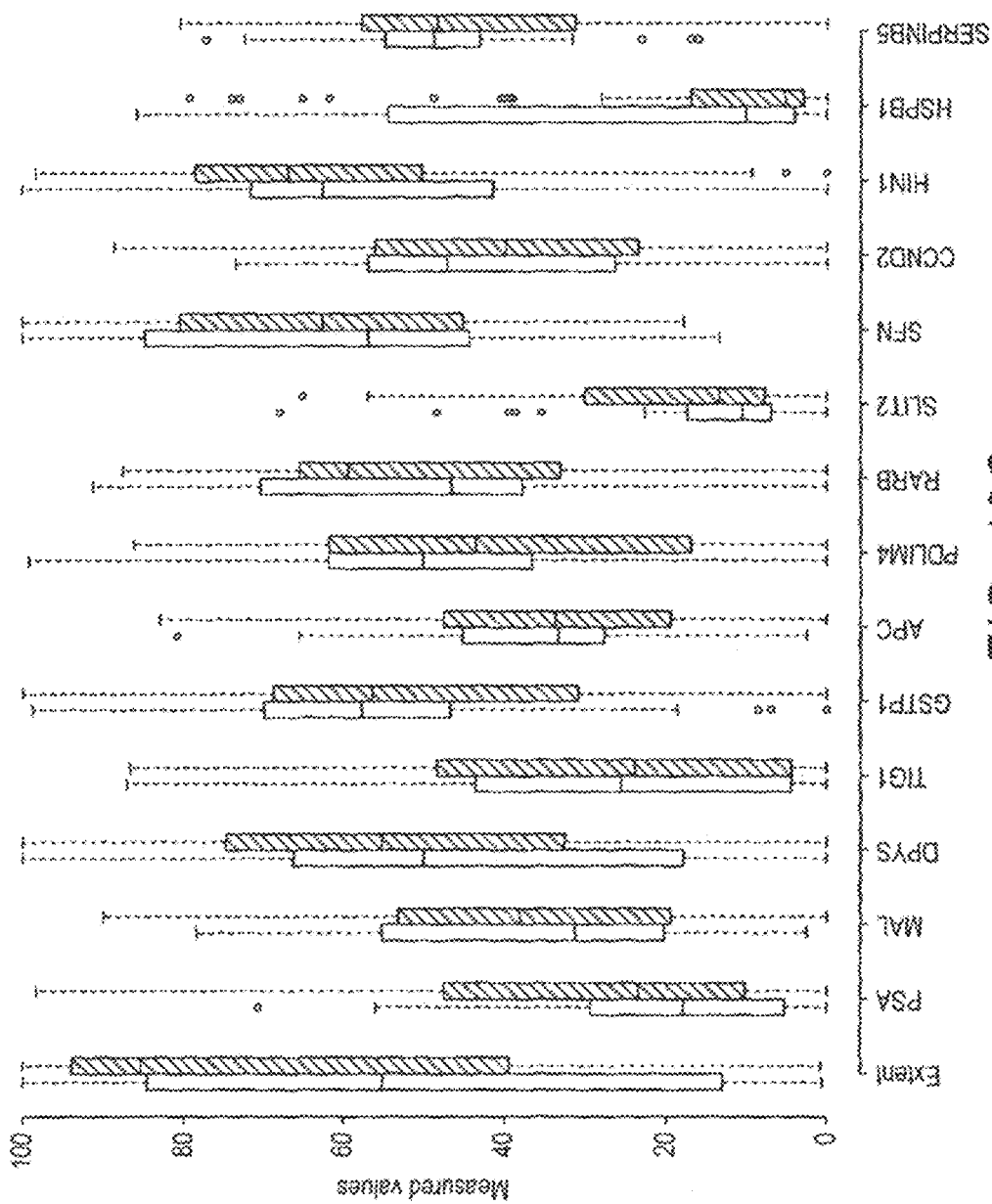

FIGS. 12A, 12B, and 12C. Distribution of methylation in A) Men with gleason score <7, B) =7 and C) >7. Men who died of prostate cancer (white box) were compared to censored men who were alive at the last visit or died of other causes (grey box). Whiskers of the boxplot mark the 5th and 95th percentiles, the box 25th percentile, median and 75 percentile, while extreme values are shown by (•).

MATERIAL AND METHODS

Human Prostate Tissue Specimens and Cell Lines

The biopsies included fresh frozen prostate tissue from 77 patients of which 48 were diagnosed with cancer and 29 with BPH. Specimens were collected either after radical prostatectomy, transurethral resection of the prostate (TURP) or TURP in cancer patients (channel TURP). The material was used and described in detail in a previous study (Vasiljevic et al Disease Markers, 30: 151-61, 2011). All specimens were centrally reviewed to confirm diagnosis by expert genitourinary pathologists (DB, YY). Gleason grading was performed by modern standardized criteria (Epstein et al Am J Surg Pathol, 29: 1228-42, 2005). In addition, formalin-fixed paraffin-embedded (FFPE) specimens of 30 men with BPH collected after TURP at St Bartholomew's Hospital, London during the period 2003-2005 were included. FFPE PCa biopsies from a defined subset of 388 patients were randomly selected from a large cohort with transurethral resection of prostate of well-characterized men residing in the United Kingdom—the so called Transatlantic Prostate Group (TAPG) cohort as previously described (Cuzick et al Br J Cancer, 95: 1186-94, 2006., Cuzick et al Lancet Oncol, 12: 245-55, 2011). 16 patients were excluded due to poor DNA quality and in 5 patients the sections consisted of only normal tissue, leaving 367 patient specimens eligible for study (Table 1). All specimens for the study were obtained from patients under informed consent. UK national ethical approval was obtained from the Northern Multicentre Research Ethics Committee, followed by local ethics committee approvals from each of the collaborating hospital trusts. Human prostate cell lines obtained from ATCC were the PNT2 immortalized prostate epithelial cell line, the hormone sensitive cancer cell lines LNCaP and VCaP and the hormone resistant, strong tumorigenic cancer cell lines, DU145, PC3, PC3M and PC3M3 as well as PC3M variant cell line ST3 with silenced RLP19. Cell lines were cultured as previously described (Ya et al Genes & Cancer, 1: 444-464, 2010). VCaP cell line was authenticated by 16 marker standard STR test May 2011. For authentication of remaining cell lines, Western blotting using both monoclonal and polyclonal antibodies against standard range of antigens was employed as well as gene expression arrays using the Agilent 64K array. All cell lines are checked on regular basis for mycoplasma infection.

DNA Extraction and Bisulfite Conversion

DNA from frozen tissues was extracted and bisulfite converted as previously described (Vasiljevic et al Disease Markers, 30: 151-61, 2011). FFPE sections were deparaffinized in xylene by submersion two times for 5 minutes and rehydrated in absolute ethanol three times for 5 minutes. From each case an H&E stained section was annotated for cancerous and normal areas by an expert pathologist (DB). Using the annotated section as a guide and depending on estimated tumour tissue size, one to six 5 μm FFPE sections were macro-dissected (Mao et al Cancer Res, 70, 2010). DNA was extracted using the QIAamp DNA FFPE tissue kit (Qiagen Inc., Hilden, Germany) according to manufacturer's recommendation with the Proteinase K digestion done overnight and finally the DNA eluted twice into a total of 80 μl of buffer ATE. 120 ng of DNA was used in the bisulfite conversion with the EpiTect Bisulfite kit (Qiagen) according to manufacturer's instructions for DNA extracted from FFPE tissues.

PCR and Pyrosequencing

HSPB1 (NCBI NT_007933.5) is located on human chromosome 7 and is composed of three exons and two introns spanning 1461 bp. 5 CpG islands were identified when the entire gene sequence including 500 bp upstream of the first exon was searched using MethPrimer (Li, L. C., and Dahiya, R. Bioinformatics, 18: 1427-31, 2002) at the default parameters (FIG. 1A). Using PyroMark Assay Design software version 2.0.1.15 (Qiagen), assays 1 to 5 were designed to cover all CpG islands (Table 2) except the last one, where we were not able to obtain a functioning assay. However, an additional assay 6 was designed downstream of the gene. Assay 2 and Assay 3 cover CG positions overlapping transcription factor binding sites (TFBS) in the 200 bp region previously shown to control HSPB1 transcription (Oesterreich et al Biochem Biophys Res Commun, 222: 155-63, 1996.). All assays were designed to cover as short an amplicon as possible including three to six CG positions (Table 2) and a non-CG cytosine internal control where possible. Due care was taken to avoid any primer overlapping CG dyads to prevent amplification biases. PCRs were performed using a converted DNA equivalent of 1000 cells (assuming 6.6 pg DNA per diploid cell) with DNA extracted from FFPE tissues and 400 cells from frozen tissues employing the PyroMark PCR kit (Qiagen). The annealing temperature for each assay is presented in Table 2, and the PCR method has been previously described (Vasiljevic et al Disease Markers, 30: 151-61, 2011). The amplified DNA was confirmed by QIAxcel capillary electrophoresis instrument (Qiagen). Pyromark and PyroGold reagents (Qiagen) were used for the pyrosequencing reaction and the signal was analyzed using the PSQ 96MA system (Biotage, Uppsala, Sweden) (Vasiljevic et al Disease Markers, 30: 151-61, 2011.). All runs contained standard curves as previously described (Vasiljevic et al Disease Markers, 30: 151-61, 2011).

Hsp-27 Expression

The Hsp-27 expression in cell lines was demonstrated with western blot and intensity was measured as previously described (Ya et al Genes & Cancer, 1: 444-464, 2010.). In the cohort FFPE material the Hsp-27 expression was previously evaluated by immunohistochemistry (IHC) of tissue microarrays (Foster et al Br J Cancer, 101: 1137-44, 2009).

Statistical Analysis

Mean methylation of the investigated CG positions within each assay was used for all analysis. To limit numbers of assays run, and costs, all assays were initially run on a selected set of specimens (FIGS. 1A and 1B), then a single PCR assay 5 was chosen to further measure DNAme in all available FFPE and fresh frozen tissues. All analyses were based on a statistical analysis plan agreed prior to analysis. Methylation data were adjusted for primer bias for assay 5 through re-scaling methylation measurements by the median standard curve. Data from FFPE tissues was modified by setting all DNAme values below 5% to 0 while remaining data was left continuous. This modification was done to lower the effect of method noise on the results; 5% DNAme was used as the positive threshold because this value clearly separated all BPH from PCa. Cuzick and Cochran Armitage trend tests were used to investigate the trend of methylation status across the six assays in continuous and dichotomised data, respectively. The Wilcoxon rank sum test was used for comparisons of DNAme from different assays in BPH vs. PCa. The Wilcoxon test was used to compare association of DNAme to Hsp-27 expression in the FFPE samples, as well as to available clinical variables. Association of HSPB1 DNAme and other variables with the secular outcome of death from PCa was investigated by Cox proportional hazards modelling. A multivariate Cox regression model was fitted to evaluate the prognostic potential of DNAme. All p values are exact and a 2-sided P-value <0.05 was regarded as significant. Statistical analyses were performed in Stata version 11 and R version 2.12.2. Graphpad Prism v5.03 was used for the illustrations.

Results

Methylation of Different Regions of the HSPB1 Gene

Methylation of CpG islands in promoter, exon1 and intron1 increased in the PCa while the corresponding regions in BPH tissue were less than 5% methylated (FIGS. 1A and 1B). DNAme investigating CGs most distal to transcriptional start site in assay 1 (Hickey et al Nucleic Acids Res, 14: 4127-45, 1986.), could not separate BPH from PCa (p=0.05). Assay 2 covering TFBS showed some separation of these categories with a low median methylation of 3% in BPH and 5% in PCa (p=0.009). In assay 3, interrogating CG positions close to the TATA box in the promoter/exon1, the median methylation increased in PCa to 5% compared to a 1% methylation in BPH (p=0.001). The increasing methylation trend in PCa continued into intron 1 as the median methylation was 8% in assay 4 (p=0.0004) and 28% in assay 5 (p<0.0001), while 0% was observed in BPH on both assays. In each PCa case where DNAme was high in Assay 5, an increasing trend in the 3' direction was also observed with corresponding assays 1-4. Assay 6, downstream of the gene, revealed high methylation in both BPH and PCa with median 52% and 68% respectively (p=0.03) (FIG. 1B). The increase in DNAme across the six assays was highly significant investigating both continuous and dichotomised data at 5% (p<0.0001).

Diagnostic Potential of HPSB1 Methylation in Frozen and FFPE Tissues

Because the difference in methylation between PCa and BPH tissues was highest when measured with assay 5 (FIGS. 1A and 1B), we used it to measure methylation in all available frozen and FFPE PCa and BPH tissues and explore the diagnostic potential of this assay. HSPB1 methylation was successfully measured in 349 of 367 FFPE TAPG cohort specimens, in 29 of the 30 FFPE BPH and all available frozen tissues. In the fresh frozen material, the median of unmodified methylation was 14% in PCa and 1% in BPH (p<0.0001) while in the FFPE material, the median unmodified methylation in PCa was 5% and 1% in BPH (p<0.0001) (FIGS. 2A and 2B). The seemingly lower methylation in FFPE PCa comparing to frozen PCa tissues was not significant (p=0.14). Using 5% as a predefined methylation threshold to minimise false positive results revealed that 56% of PCa cases scored as positive, while none of the BPH were positive. At the same threshold, sensitivity in the FFPE material was 50% [95% CI 45-56%] and specificity 100% [95% CI 88-100%] (FIG. 2B).

Exploratory Study of Associations Between of HSPB1 DNAme and Clinical Variables

The median age of patients in the TAPG cohort was 70.5 years (interquartile range 67.3 to 73.2). Median follow up was 9.5 years with up to a maximum 20 years of follow up, where 91 patients died of PCa (DPCa). The summary statistics of clinical and pathological variables are presented in Table 1. Univariate Cox modelling indicated a highly significant association between DPCa and Gleason score, extent of disease (proportion of TURP chips with disease), PSA level and Ki67, whereas age and HSPB1 DNAme level showed a weaker but significant association (Table 1). The hazard ratio (HR) per 50% increase of HSPB1 DNAme was 1.77 [95% CI 1.13-2.79]. In addition, the stratified hazard ratio over time (FIG. 3) suggested that HSPB1 methylation has a strong effect as a prognostic gene after approximately 7 years post-diagnosis.

We further investigated the relationship among HSPB1 DNAme and all available variables.

There was no association between HSPB1 DNAme and age (p=0.2) or PSA (p=0.07), but a significant association to Gleason score (p=0.003) and extent of disease (p<0.0001) (FIGS. 6A, 6B, 6C, 6D, 6E, and 6F). Due to the strong association, in the multivariate analysis a combined variable where Gleason score was multiplied with modified HSPB1 DNAme was included. Furthermore, all variables significant in the univariate model were taken into the multivariate analysis except for extent of disease and Ki67. Extent of disease was excluded due to the fact that with advent of PSA screening, men are normally diagnosed by needle biopsies rather than TURP and therefore this variable would not be available for risk assessment. Ki67 score was excluded due to a large number of missing values. Gleason score* modified HSPB1 DNAme had HR 0.985 (CI95% 0.97-0.99) and together with modified HSPB1 DNAme, PSA and Gleason score formed a final multivariate model (Table 3.). A statistically significant negative interaction between modified HSPB1 and Gleason score was found, indicating that individuals with low Gleason score and high methylation levels of HSPB have a significantly increased risk of aggressive disease than men with low HSPB and similar PSA levels (FIGS. 6A, 6B, 6C, 6D, 6E, and 6F).

DNAme of HSPB1 and Expression of Hsp-27

The expression of Hsp-27 and DNAme of HSPB1 were measured in 8 cell lines (FIGS. 4A and 4B). Expression of Hsp-27 was higher in LnCaP (1.7) compared to PNT2 (1), while the expression was lowest in PC3M-3 and absent in VCaP. DU145, PC3, PCM3 and ST3 displayed similar levels of expression to that in PNT2 (FIG. 4A). The highest methylation of HSPB1 was measured in VCaP cells with assay 4, 5 and 6 (>90%), consistent with DNAme suppressing expression of the protein. Furthermore, assay 6 measured 60-100% methylation in all cell lines, except LnCaP, where methylation was 40% and also highest Hsp-27 expression was observed in this cell line (FIG. 4B). In FFPE tissues, DNAme levels showed no association to the Hsp-27 IHC score with the Wilcoxon test (p=0.6)

Discussion

It is recognised that the level of Hsp-27 protein within the malignant PCa cells may be significantly different between the original in-situ location and invasive location. The level of this latter expression appears to be profoundly important with respect to the phenotypic behaviour of an individual PCa where re-expression of Hsp-27 predicts aggressive behaviour (Foster et al Br J Cancer, 101: 1137-44, 2009). Presently, the mechanism that determines the level of Hsp-27 expression is unknown. A generally proposed mechanism for the role of DNAme during carcinogenesis is that both hypo- and hypermethylation may occur, thereby disrupting the chromatin structure and transcription of tumour suppressors and oncogenes, which results in an unbalanced cellular milieu. In PCa, substantial research efforts have shown that detection of increased DNAme of the promoters of genes such as GSTP1, RARB, APC, TIG1 and many more can be detected in biopsies as well as bodily fluids and may therefore be useful for early detection and prognosis, but none have so far been validated for routine clinical use (Bastian et al Eur Urol, 46: 698-708, 2004). In the current study, we report for the first time the methylation status of CpG islands within the HSPB1 gene in prostate cell lines as well as BPH and PCa tissue. The methylation increased in the 3' direction, beginning with CG positions covering the TFBS in PCa but not BPH (FIG. 1B). Unsurprisingly, DNAme measured highest (45 to 70%) in CG positions outside of the CpG islands downstream of the gene in both BPH and PCa; however differences in DNAme still remained significantly (p=0.03) higher in PCa than BPH suggesting that DNA methylation outside CpG islands also may have diagnostic or prognostic significance (FIG. 1B). Furthermore, the observed increase in DNAme in cancer tissue could reflect a generalized cellular defence attempt to inhibit expression of potentially destabilizing genes through a global increase of de novo methylation (Nguyen et al J Natl Cancer Inst, 93: 1465-72, 2001). DNAme in seven of the human prostate cell lines was overall low (<10%) in promoter/exon and intron CG positions. Only VCaP showed a similar gradual DNAme increase across the gene to that seen in PCa tissues, measuring from 60% in promoter/exon1 to 100% in the intron (FIG. 4B). These cells were also the only ones among 8 cell lines of varying malignancy that were negative for Hsp-27 expression, suggesting silencing of the gene by hypermethylation. Expression of Hsp-27 protein in the benign PNT2 cell line was set as the reference to compare the relative expression in the hormone sensitive cancer cell lines LNCaP, VCaP and the hormone resistant, strong tumorigenic cell lines, DU145, PC3, PC3M and PC3M3 as well as PC3M variant cell line ST3. The Hsp-27 expression was highest in LnCap, however no difference in DNAme within the gene was seen comparing to the PNT2 cell line (FIGS. 4A and 4B). Furthermore, in PC3M3 the expression was decreased to half but the gene was unmethylated, while assay 6 was lower than that in PNT2 cells. This suggests that the expression of Hsp-27 is either only partly controlled by DNAme or possibly other mechanisms. Additionally, absence of correlation between DNAme and Hsp-27 expression in patient samples (FIGS. 6A, 6B, 6C, 6D, 6E, and F) is inconsistent with the control of Hsp-27 protein levels in vivo by DNAme.

In order to assess the diagnostic potential of HSPB1 methylation, we compared the methylation differences between BPH and PCa in 77 frozen tissues and 378 FFPE tissues (FIGS. 2A and 2B). We believe that measuring of DNAme with assay 5 alone provided sufficient assessment as the other assays, tested in the initial subset of patients (FIGS. 1A and 1B), showed readily evident increasing trend of methylation in 3' direction of the gene and therefore it is likely that measuring methylation levels with the other assays would not have yielded any different or additional results. At a cut-off of 5% methylation, estimated to minimise false positive detection, 56% of the frozen-biopsy PCa were correctly classified while none of the BPH were misclassified. Highly similar results were seen in the FFPE tissues, where the sensitivity was 50% and specificity 100% at a 5% DNAme cut-off (FIG. 2A). Taking into account our previous report of aberrant methylation in 20 genes, as well as other reports within the field, there are numerous other genes including RARB and GSTP1 that show a much stronger potential than HSPB1 as diagnostic biomarkers in PCa (Vasiljevic et al Disease Markers, 30: 151-61, 2011, Phe et al BJU Int, 105 1364-70, 2010).

In the TAPG cohort of patients, previous studies have indicated the prognostic potential of several clinical variables including Gleason score, PSA (O'Brien et al Int J Cancer, 10: 2373-81, 2011), CCP score (Cuzick et al Lancet Oncol, 12: 245-55, 2011), Hsp-27 score (Foster et al Br J Cancer, 101: 1137-44, 2009) and others. However in our study, the univariate Cox model (Table 1) showed no association between HSP-27 expression and DPCa. This may be due to lack of sufficient power as we did not study the same large set of specimens. Also, in the earlier study (Foster et al Br J Cancer, 101: 1137-44, 2009) the association between overexpression and death was shown predominantly in the subset of men who did not have ERG rearrangements, a variable not investigated in the current study. The prognostic value of HSPB1 DNAme was indicated by both univariate and multivariate models. According to the univariate model, the hazard ratio increased with factor 1.12 for every ten percent increase or DNAme or 1.77 for a 50% increment. Interestingly, the stratified hazard ratios over time as well as Kaplan Meier survival analysis suggested that HSPB1 methylation has a strong effect as a prognostic gene after approximately 7 years post-diagnosis (FIG. 3 and FIG. 7). Previous studies employing IHC staining of Hsp-27 (Foster et al Br J Cancer, 101: 1137-44, 2009.) showed that expression was weaker in precursor lesions compared to the benign tissues as well as more aggressive PCa suggesting a reactivation of Hsp-27 expression.

In combination, the IHC and DNAme data suggest a possible extension of this mechanism, where early DNAme-independent shutoff of Hsp-27 is an early event in carcinogenesis and then a subset of the Hsp-27 reactivated aggressive PCa may become repressed by DNAme of HSPB1. These men may be of lower risk but they still have PCa of greater risk for an early death than men who have neither Hsp-27 overexpression nor elevated DNAme of the HSPB1 gene. Further, our data showed that DNAme of HSPB1 was strongly correlated to Gleason score (p<0.003). Taking into account the strong correlation, a combined variable was included in a multivariate model where the combined variable was found negatively correlated to DPca. Overall, our results suggest that HSPB1 DNAme is a marker of poor outcome in men who have a low Gleason score and who would otherwise be regarded as of low risk (FIG. 7). Additionally, in the multivariate analysis HSPB1 methylation alone as well as Gleason score*HSPB1 methylation formed a final model with the two strongest prognostic variables PSA and Gleason score. A limitation of our study is the use of TURP specimens and we recognize that these do not represent current practice for the diagnosis of prostate cancer; however, it was the only way to assemble a cohort with 20 years of follow-up as TURPs were the standard in the 1990s. We believe that HSPB1 will give similar data in prostate needles (preliminary data) although the terms of the risk equation may change to reflect the different specimen types. Studies to validate HSPB1 in needle biopsies are now underway.

In conclusion, HSPB1 is essentially unmethylated in BPH where it encodes a protein that is strongly expressed in the cytoplasm of the luminal and basal epithelial cells. However, in PCa, the gene is increasingly methylated proceeding in the 3' direction from the end of promoter, through the exon1 and intron1 regions. At a 5% methylation cut-off, HSPB1 methylation has 100% specificity and 50% diagnostic sensitivity for PCa. Methylation within the HSPB1 gene is associated with late occurring poor outcome in PCa and is strongly associated with other surrogate markers of poor outcome such as high Gleason score and high PSA. Although the prognostic value of HSPB1 for death from PCa is weaker than PSA and Gleason score, it brings additional information and therefore the utility in combination is worth further evaluation.

DNA Methylation Gene-Based Models Indicating Independent Poor Outcome in Prostate Cancer In prostate cancer, numerous genes have been found aberrantly hypermethylated, with GSTP1, APC1 and RARB amongst the most frequently reported (Nelson W G, Yegnasubramanian S, Agoston A T, et al. Front Biosci 2007; 12: 4254-4266). Assessment of changes in methylation has mostly been investigated for diagnostic purposes. Moreover, a majority of the studies focusing on prognostic value of methylation have the time to biochemical reoccurrence after surgical treatment as primary endpoint, which does not accurately estimate the potential of the cancer in terms of risk of death if left untreated (Vanaja D K, Ehrich M, Van den Boom D, et al. Cancer Invest 2009; 27: 549-560, Banez L L, Sun L, van Leenders G J, et al. J Urol 2010; 184: 149-156, Liu L, Kron K J, Pethe V V, et al. Int J Cancer 2011; 129: 2454-2462). The aim of our study was to assess the prognostic biomarker potential of DNA methylation of 13 candidate genes univariately and in combination with the currently employed clinicopathologic parameters of prostate cancer progression. We selected GSTP1, APC, RARB, CCND2, SLIT2, SFN, SERPINB5, MAL, DPYS, TIG1, HIN1, PDLIM4 and HSPB1 as candidate genes.

Methods

Study Population

Full details of the TAPG cohort have been described previously (Cuzick J, Fisher G, Kattan M W, et al. Br J Cancer 2006; 95: 1186-1194). In summary, prostate cancers were identified from six cancer registries in Great Britain and FFPE blocks were obtained from the pathology departments of the collaborating hospitals. Men were included if they were younger than 76 years at the time of diagnosis, had a baseline PSA measurement less than 100 ng/ml and had clinically localised prostate cancer diagnosed by TURP between 1990 and 1996, inclusive. Baseline PSA concentration was defined as the last PSA concentration within 6 months of diagnosis, including pre-diagnostic concentrations, and at least 3 weeks after any biopsy. Extent of disease was determined by a microscopic inspection of TURP chips by a trained pathologist (DB) who determined the overall percentage of cancer visible in each set of biopsies. Samples were excluded from men treated with radical prostatectomy, radiation therapy, hormone therapy, as well as those who showed evidence of metastatic disease, or died within 6 months of diagnosis. The original histological specimens from the TURP procedure were reviewed centrally by a panel of expert urological pathologists to confirm the diagnosis and, when necessary, to reassign scores by use of a contemporary interpretation of the Gleason scoring system (Glinsky G V, Glinskii A B, Stephenson A J, et al. J Clin Invest 2004; 113: 913-923). Follow-up was through the cancer registries and the last review took place in December 2009. Our endpoint of interest was death from prostate cancer defined according to WHO's standardised criteria (Parkin D M, Whelan S L, Ferlay J, et al. IARC scientific publication no 155 2002). National ethics approval was obtained from the Northern Multicentre Research Ethics Committee, followed by local ethics committee approval at each of the collaborating hospitals (Cuzick J, Fisher G, Kattan M W, et al. Br J Cancer 2006; 95: 1186-1194).

DNA Isolation and Bisulfite Conversion

FFPE TURPs were obtained from 388 patients randomly selected from the cohort. 16 patients were excluded due to poor DNA quality and in 5 patients the sections consisted of only normal tissue, leaving 367 patient specimens eligible for study. FFPE sections were deparaffinized in xylene by submersion two times for 5 minutes and absolute ethanol three times for 5 minutes. From each case an H&E stained section that had been previously annotated for cancerous and normal areas by an expert pathologist (DB) was used as a guide for macrodissection. Depending on estimated tumour tissue size, one to six 5 µm FFPE sections were dissected (Mao X, Yu Y, Boyd L K, et al. Cancer Res 2010; 70) and DNA was extracted and converted as previously described (Vasiljevic N, Ahmad A S, Beesley C, et al. Prostate Cancer Prostatic Dis 2012; 16: 35-40).

DNA Methylation Assay

The primer design, sequences and PCR conditions were previously optimised and described (Vasiljevic N, Ahmad A S, Beesley C, et al. Prostate Cancer Prostatic Dis 2012; 16: 35-40, Vasiljevic N, Wu K, Brentnall A R, et al. Disease Markers 2011; 30: 151-161). PCRs were performed employing the PyroMark PCR kit (Qiagen, Hilden Germany) with standard curves and a converted DNA equivalent of 1000 cells per specimen. Presence of the correct amplicons was confirmed by the QIAxcel capillary electrophoresis instrument (Qiagen). Pyromark and PyroGold reagents (Qiagen) were used for the pyrosequencing reaction and the raw pyrogram signals were analyzed using the PyroMark Q96 ID system (Qiagen) (Vasiljevic N, Wu K, Brentnall A R, et al. Disease Markers 2011; 30: 151-161).

Statistical Methods

The statistical methods were documented in a pre-specified statistical analysis plan and laboratory testing was blinded from the clinical variables to minimize bias in the results. Mean methylation of the investigated CpG positions within each assay was used for all analyses. The Spearman's rho correlation coefficient was estimated for methylation levels of different gene combinations as well as between each gene and age (as a continuous variable), PSA Score, Gleason Score and Extent of Disease respectively. A univariate Cox regression model with the primary endpoint of death from prostate cancer was fitted for each of the available clinical variables and each investigated gene. Patients were censored if alive or if they died from causes other than prostate cancer. P-values were adjusted for multiple comparisons using the false discovery rate approach (Benjamini Y, Hochberg Y. Journal of the Royal Statistical Society 1995; 57: 289-300). A further predefined assessment to develop the best final multivariate Cox models for genes alone and for all available variables was selected by stepwise Cox modelling (likelihood ratio (LR) test). Gene methylation values and clinical variables were analyzed as continuous data in all fitted Cox models. Kaplan Meier survival curves were plotted for the models presented. All applied tests were two-sided and p-values of ≤0.05 were regarded as statistically significant. Statistical analyses were done with STATA 11 and R 2.12.2.

Results

DNAme of 13 candidate genes—GSTP1, APC, RARB, CCND2, SLIT2, SFN, SERPINB5, MAL, DPYS, TIG1, HINT, PDLIM4 and HSPB1 was measured in 367 men from the TAPG cohort. Median age was 70.5 years (range 49.9-76, IQR=5.9), median follow-up was 9.5 years and there were 99 deaths from prostate cancer. The methylation measurements for the different genes were of varying success rate (94-99%) (Table 4). The distribution of methylation of each gene was plotted separating the two main groups: men who died of prostate cancer and men who were censored because they were alive at the last visit or died of other causes (FIG. 9). To facilitate visual comparison, the PSA values, extent of disease and Gleason score were also plotted in the same graph (FIGS. 1A and 1B). Gleason score displayed the best separation of the two groups (Wilcoxon $\chi^2$=77.26, P<0.0001), followed by extent of disease and PSA with (Wilcoxon $\chi^2$=69.54 and 69.03 respectively (P<0.0001). Among the genes, the best separation of the groups was observed with methylation of DPYS and TIG1 genes (Wilcoxon $\chi^2$=20.77 and 16.33 respectively, (P<0.0001).

Correlation between the clinical variables and gene methylation was investigated (FIG. 11). Among the clinical variables, extent of disease was most correlated to gene methylation of MAL, RARB, GSTP1, APC and DPYS with Spearman r ranging from 0.42 to 0.49 (P<0.0001). Gleason score had the strongest correlation with methylation of MAL, GSTP1 and TIG1 (r=0.38-0.43, P<0.0001) and PSA with methylation of DPYS, GSTP1 and MAL (r=0.34-0.37, P<0.0001). Age was weakly correlated to all other variables (r<0.2). Genes APC, RARB and GSTP1 showed highest correlation with methylation of other genes while SFN, HSPB1 and SERPINB5 showed lowest correlation to all other variables and genes.

The Cox univariate regression (Table 4) showed that several of the genes, namely GSTP1, MAL, DPYS and TIG1 were significantly associated to prostate cancer specific death (P<0.0001) (Table 1). In comparison, Gleason score was the strongest predictor of prostate cancer-specific death; the hazard ratio (HR) was 2.33 [95% CI 1.99-2.74] for each per unit increment (i.e. 4 . . . 10). For MAL, the HR per 10% increment in methylation was 1.28 [95% CI 1.17-1.40] (Table 4). To make clinical variables comparative to methylation, the HR for the PSA (ng/mL), extent of disease (%) and age (year) were also calculated per 10 unit increments.

Methylation was successfully measured for all 13 genes in 309 patients including 81 prostate cancer-specific deaths and this subset was used for the multivariate analysis. To assess clinical utility in differing circumstances, four distinct sets of variables were considered for identification of best multivariate model by stepwise Cox modelling. The four sets were A) Methylation only variables, B) Molecular variables (gene methylation and PSA), C) Clinical variables—current standard (Gleason score and PSA), and D) All available variables (including the interaction between the gene methylation and the clinical variables). Model D showed best predictive power with LR $\chi^2_{(6df)}=125.7$ and included Gleason score, PSA, DPYS, HSPB1, interaction term: (HSPB1× Gleason score) and CCND2 (Table 2). The model based on currently used diagnostic variables was the next best model with LR $\chi^2_{(2df)}=111.4$. Model B included PSA, DPYS, HSPB1, MAL and TIG1 with LR $\chi^2_{(5df)}=76$ and the gene-only model comprised: DPYS, GSTP1, and MAL with LR $\chi^2_{(3df)}=49.4$ (Table 2). As a higher likelihood ratio $\chi^2$ indicates a better model and the $\Delta\chi^2_{(4df)}$ between model D and C was 14.3 (P=0.006), this indicates that incorporating gene methylation improved the risk prediction (Table 5).

The risk scores obtained from the linear predictors of the four models were categorised into low, medium and high risk groups using the 25% and 75% quantiles and Kaplan Meier survivor curves were plotted (FIG. 10). The proportion of prostate cancer-specific deaths in each of the groups low, median and high were calculated for the different models (Table 6) expanding the information from the curves. Kaplan Meier survivor curves illustrated that although the models including Gleason score are best, use of PSA in combination with gene methylation provided a similar amount of information, particularly for identifying patients at highest risk (FIG. 10).

Discussion

Measuring the methylation of gene promoters/first exons appears to have prognostic value in prostate cancer with several promising biomarkers revealed in the current study. 12 of the 13 investigated genes were associated to prostate cancer-specific death with HR ranging between 1.09 and 1.28 per a decile increase in DNAme in the univariate analysis (Table 4). In comparison, the HR for Gleason score was 2.33 per unit increase in grade while the corresponding value per 10 ng/ml increase of PSA was 1.36. Gleason score was the best available prognostic variable (LR $\chi^2=105.3$), while MAL was the most prognostic among the 13 genes (LR $\chi^2=25.4$).

In biomarker research, it is important to first find and credential biomarkers in suitable cohorts (Foster C S, Cooper C S. Biomark Med 2009; 3: 329-333) and to then proceed to the validations and qualifications (Kagan J, Srivastava S, Barker P E, et al. Cancer Res 2007; 67: 4545-4549). Our study was conducted following REMARK guidelines (McShane L M, Altman D G, Sauerbrei W, et al. Breast Cancer Res Treat 2006; 100: 229-235). The use of TAPG TURP specimens allowed us to assemble a cohort of untreated men with prostate cancer with up to 20 years of follow-up, therefore this TURP cohort is a suitable set of specimens for the initial credentialing work.

Models based on gene methylation only, gene methylation in combination with PSA and gene methylation in combination with all available variables were fitted and compared to a model based on the PSA and Gleason score only (Table 5) to explore possibilities in different clinical scenarios. The extent of disease estimated from the TURP specimens was excluded in the latter model due to the fact that this variable would not be available for risk assessment in the needle biopsies typical of normal clinical settings. The model with the best prognostic ability included Gleason score, PSA, HSPB1, HSPB1× Gleason score, CCND2 and DPYS (LR $\chi^2=125.7$). Recently, we reported that HSPB1 methylation and its interaction with Gleason score has prognostic value and may be of clinical importance for risk stratification of men in the low risk (<7) Gleason score group (Vasiljevic N, Ahmad A S, Beesley C, et al. Prostate Cancer Prostatic Dis 2012; 16: 35-40). Here, in a multivariate comparison with 12 other genes, HSPB1 methylation and its interaction term with Gleason score remained important for risk stratification (Table 5). In addition, HSPB1 methylation was also significant in a model with PSA and methylation of genes: DPYS, MAL and TIG1 (Table 2) further underlining its prognostic value.

Similarly to HSPB1, CCND2 methylation displayed an HR of 0.86 [95% CI 0.75-0.98] (Table 5). Also, in a subset of men with Gleason score 7, median methylation of CCND2 was lower in men who died of prostate cancer (FIGS. 12A, 12B, and 12C). This indicated that methylation of CCND2 may be important for identifying men at high risk of prostate cancer-specific death in the medium (=7) Gleason group. Previously, the prognostic value of CCND2 had been only evaluated with respect to biochemical reoccurrence but with discordant findings (Henrique R, Ribeiro F R, Fonseca D, et al. Clin Cancer Res 2007; 13: 6122-6129, Rosenbaum E, Hogue M O, Cohen Y, et al. Clin Cancer Res 2005; 11: 8321-8325).

DPYS appeared useful for predicting prostate cancer-specific mortality in the gene-based models (Table 5). Also, the distribution of methylation (FIG. 9) showed the largest difference in median methylation between the two groups of patients. Although aberrant methylation of DPYS has been reported by us and others (Vasiljevic N, Wu K, Brentnall A R, et al. Disease Markers 2011; 30: 151-161, Chung W, Kwabi-Addo B, lttmann M, et al. PLoS One 2008; 3: e2079) this is the first report demonstrating its prognostic value.

In particular, we were interested to examine the difference in survival prediction capabilities between the model based on the current clinical reference standard (i.e. PSA and Gleason score) when compared to a PSA and gene methylation model because this approach could be used to triage men to biopsy, similar to the proposed use for PCA3 (van Poppel H, Haese A, Graefen M, et al. BJU Int 2012; 109: 360-366). Substantial research efforts have shown that detection of increased DNA methylation can be detected in bodily fluids. (Bastian P J, Yegnasubramanian S, Palapattu G S, et al. Eur Urol 2004; 46: 698-708, Ellinger J, Muller S C, Stadler T C, et al. Urol Oncol 2009; 29: 124-129) Therefore, if validated, a combination test on bodily fluids could realistically reduce health care burden and spare men from invasive examinations and potentially hazardous biopsies. Comparing the PSA-Gleason score with PSA-gene methylation model, a similar proportion of men were classed in the low, medium and high risk groups (FIG. 10). The proportion of men who died in each of the groups (Table 6) showed a modest decrease in sensitivity of PSA-gene model compared to the PSA-Gleason model. Specificity was however similar and therefore assessing DNA methylation in bodily fluids deserves to be explored. Prior to such experiments, a validation of the current PSA and gene model is needed in a cohort comprising of needle biopsies to eliminate any biases introduced by use of TURP tissues.

In a previous study where prostate cancer-specific death was also the study endpoint, methylation of APC had prognostic potential in contrast to GSTP1 methylation (Richiardi L, Fiano V, Vizzini L, et al. J Clin Oncol 2009; 27: 3161-3168). In our univariate analysis, APC methylation was significant (p=0.002), but did not form any of the multivariate models (Table 5) while GSTP1 DNAme showed prognostic potential (Table 4) in the univariate analysis as well as the multivariate gene-only model (P=0.01) (Table 5). A plausible explanation for the discrepancy between studies is that only Gleason score was available in the previous study and perhaps also that a non-quantitative method (methylation-specific PCR) was used.

Moreover, we demonstrated that APC and GSTP1 DNAme were strongly correlated to methylation of other genes (FIG. 11). In fact, methylation of most genes is moderately correlated indicating a generalized process of methylation remodelling in the cancer cell genome. Therefore, it is possible that the strong correlation among variables would eliminate a variable (e.g. APC) that appears strong in univariate analysis if another stronger one (e.g. GSTP1) was included in the multivariate analysis.

Currently, Gleason score and baseline PSA concentration are the strongest predictors. Results from the univariate analysis have shown that the genes individually were only modest predictors of death from prostate cancer (Table 4). However, the multivariate analysis indicated that the methylation of genes DPYS, CCND2 and HSPB1 added a substantial amount of prognostic information not captured by any other measure. Consequently, the gene score allowed more accurate prediction of those men who can be safely managed by watchful waiting, and, of equal importance, which men with apparently low-risk disease are actually are at high risk of death from prostate cancer and might benefit from immediate treatment. A methylation test on bodily fluids may improve identification of men who are in need of biopsy.

In conclusion, DNA assays for methylation of HSPB1, CCND2, MAL and TIG1 have potential to improve the approach to managing prostate cancer.

TABLE 1-continued

|  | No of observations | DPca | HR (95% CI) | p-value |
|---|---|---|---|---|
| ≤6 | 108 | 10 | | |
| >6-20 | 89 | 11 | | |
| >20-40 | 55 | 16 | | |
| >40-75 | 44 | 17 | | |
| >75-100 | 65 | 43 | | |
| PSA | 367 | 99 | 2.024 (1.737, 2.358) | <0.0001 |
| ≤4 | 138 | 14 | | |
| >4-10 | 76 | 11 | | |
| >10-25 | 73 | 25 | | |
| >25-50 | 54 | 28 | | |
| >50-100 | 26 | 21 | | |
| HSP27 Score | 233 | 68 | 1.529 (0.872, 2.680) | 0.154 |
| negative | 187 | 52 | | |
| positive | 46 | 16 | | |
| Ki67 IHC | 306 | 86 | 2.984 (1.934, 4.604) | 3.06e-06 |
| ≤5 | 238 | 52 | | |
| >5 | 68 | 34 | | |
| HSPB1[b] methylation | 349 | 91 | 1.12 (1.02, 1.21) | 0.020 |

TABLE 2

| | Gene region | Primer name | Sequence 5'→3' | Size (bp[a]) | Position in the gene[b] | No of CG sites | Annealing Temp(°) | SEQ ID NO: |
|---|---|---|---|---|---|---|---|---|
| Assay 1 | promoter | HSP27p1F (b) HSP27p1R HSP27p1s | AGTTTTTATTTGGAATTTTTTT B[c]-CAACCTATCTAACTCTATCCT GTTAAGGAAAGTAAATGAATT | 170 | CpG island 1 -216--46 | 6 | 48 | SEQ ID NO: 1 |
| Assay 2 | promoter | HSP27p7F (b) HSP27p7R HSP27p7s | AGAGAAGGTTTTAGATGAGGGTTGAA B-CCCCTCCCCATACACTCC GATGAGGGTTGAATTTTT | 83 | CpG island 1 -70-13 | 4 | 56 | SEQ ID NO: 2 |
| Assay 3 | Promoter/ exon | HSP27p6F (b) HSP27p6R HSP27p6s | GGTTATGTTGGTTGATTTTGT B-AATCATTACCATTAATAAAAACCTCA TGGTTGATTTTGTTTTGGA | 134 | CpG island 2 27-161 | 5 | 54 | SEQ ID NO: 3 |
| Assay 4 | intron | HSP27p3F (b) HSP27p3R HSP27p3s | ATCTTAAACTCCTAACCTCAAAC B-TTTTTTTGTTTAGGAATTGGGAGTG TTTGTTTAGGAATTGGGAGT | 111 | CpG island 3 662-773 | 3 | 53 | SEQ ID NO: 4 |
| Assay 5 | intron | HSP27p4F (b) HSP27p4R HSP27p4s | AGTTGGGGAGTGAGTAGT B-CAACCCCATCCCCAAATAA TGGGGAGTGAGTAGTA | 112 | CpG island 4 912-1024 | 5 | 54 | SEQ ID NO: 5 |
| Assay 6 | | HSP27p9F (b) HSP27p9R HSP27p9s | ATTTTGTAGTTTTTGGGTTTTTAAGT B-AATCACCATCCCAATCACCTT TTTGGGTTTTTAAGTTGGGT | 62 | Not CpG island 1532-1594 | 3 | 52 | SEQ ID NO: 6 |

TABLE 3

| variable | X² | d.f. | P-value |
|---|---|---|---|
| modified HSPB1 | 6.582 | 2 | 0.037 |
| Gleason Score | 38.420 | 2 | <0.0001 |
| PSA Score | 28.094 | 1 | <0.0001 |
| dicotomised Age | 0.227 | 1 | 0.634 |
| modified HSPB * GleasonScore | 6.579 | 1 | 0.010 |
| Total | 102.211 | 7 | 0.000 |

TABLE 1

|  | No of observations | DPca | HR (95% CI) | p-value |
|---|---|---|---|---|
| Age | 367 | 99 | 1.838 (1.023, 3.300) | 0.029 |
| ≤65 | 63 | 13 | | |
| >65 | 304 | 86 | | |
| Gleason Score | 367 | 99 | 3.092 (2.417, 3.956) | <0.0001 |
| <7 | 191 | 19 | | |
| =7 | 84 | 27 | | |
| >7 | 92 | 53 | | |
| Cancer in biopsy (%) | 361[a] | 97 | 1.911 (1.653, 2.209) | <0.0001 |

TABLE 4

| | HR[A] (95% CI) | LR[B] $X^2$ | ADJUSTED[C] P-VALUE | C-INDEX | TOTAL NO[D] | EVENT NO[E] |
|---|---|---|---|---|---|---|
| GLEASON SCORE | 2.33 (1.99, 2.73) | 105.3 | $2.2 * 10^{-16}$ | 0.79 | 367 | 99 |
| EXTENT OF DISEASE | 1.27 (1.21, 1.34) | 80.1 | $2.2 * 10^{-16}$ | 0.76 | 367 | 99 |
| PSA | 1.36 (1.28, 1.45) | 68.9 | $6.3 * 10^{-16}$ | 0.76 | 367 | 99 |
| AGE | 1.04 (1.00, 1.09) | 3.2 | 0.08 | 0.52 | 367 | 99 |
| MAL | 1.28 (1.17, 1.40) | 25.4 | $2.0 * 10^{-6}$ | 0.64 | 352 | 95 |
| DPYS | 1.20 (1.12, 1.29) | 24.2 | $2.9 * 10^{-6}$ | 0.65 | 344 | 95 |
| TIG1 | 1.25 (1.14, 1.36) | 20.9 | $1.4 * 10^{-5}$ | 0.65 | 350 | 90 |
| GSTP1 | 1.17 (1.08, 1.26) | 16.4 | $1.2 * 10^{-4}$ | 0.62 | 357 | 98 |
| APC | 1.18 (1.08, 1.29) | 10.9 | 0.002 | 0.61 | 365 | 99 |
| PDLIM4 | 1.16 (1.06, 1.26) | 10.9 | 0.002 | 0.60 | 365 | 98 |
| RARB | 1.13 (1.04, 1.24) | 7.7 | 0.01 | 0.60 | 351 | 98 |
| SLIT2 | 1.17 (1.05, 1.31) | 6.6 | 0.016 | 0.58 | 350 | 94 |
| SFN | 1.13 (1.02, 1.25) | 5.8 | 0.023 | 0.57 | 363 | 99 |
| CCND2 | 1.12 (1.02, 1.23) | 5.2 | 0.029 | 0.56 | 364 | 99 |
| HIN1 | 1.09 (1.01, 1.18) | 5.1 | 0.029 | 0.59 | 350 | 97 |
| HSPB1 | 1.12 (1.02, 1.22) | 5.0 | 0.029 | 0.52 | 349 | 91 |
| SERPINB5 | 0.95 (0.83, 1.08) | 0.7 | 0.408 | 0.53 | 357 | 95 |

TABLE 5

| | MODEL A: GENE-ONLY | | | MODEL B: GENES + PSA | | | MODEL C: GLEASON + PSA | | | MODEL D: FULL MODEL | | |
|---|---|---|---|---|---|---|---|---|---|---|---|---|
| VARIABLE | HR (95% CI) | $X^2$ | P-VALUE | HR (95% CI) | $X^2$ | P-VALUE | HR (95% CI) | $X^2$ | P-VALUE | HR (95% CI) | $X^2$ | P-VALUE |
| GLEASON | —[B] | — | — | — | — | — | 2.20 (1.82, 2.67) | 66.3 | $3.3 * 10^{-16}$ | 2.72 (2.09, 3.53) | 56.3 | $6.2 * 10^{-14}$ |
| PSA | — | — | — | 1.27 (1.18, 1.38) | 36.5 | $1.5 * 10^{-9}$ | 1.27 (1.17, 1.37) | 34.9 | $3.5 * 10^{-9}$ | 1.23 (1.14, 1.34) | 24.7 | $6.7 * 10^{-7}$ |
| DPYS | 1.12 (1.02, 1.24) | 5.8 | 0.016 | 1.12 (1.02, 1.24) | 5.3 | 0.021 | — | — | — | 1.13 (1.03, 1.25) | 6.4 | 0.012 |
| HSPB1 | | | | 0.88 (0.79, 0.99) | 4.6 | 0.032 | — | — | — | 2.39 (1.15, 4.97) | 5.5 | 0.019 |
| GLEASON × HSPB1[A] | — | | | — | | | — | — | — | 0.89 (0.81, 0.98) | 6.2 | 0.012 |
| CCND2 | | | | | | | — | — | — | 0.86 (0.75, 0.98) | 5.1 | 0.024 |
| MAL | 1.19 (1.05, 1.34) | 7.6 | 0.006 | 1.17 (1.03, 1.34) | 5.7 | 0.017 | — | — | — | | | |
| GSTP1 | 1.15 (1.03, 1.27) | 6.6 | 0.010 | | | | — | — | — | | | |
| TIG1 | | | | 1.15 (1.03, 1.27) | 6.5 | 0.011 | — | — | — | | | |
| LR $X^2$ (DF) | 49.4 (3) | | | 76.6 (5) | | | 111.4 (2) | | | 125.7 (6) | | |

TABLE 6

| Model[a] | $X^2$ | Low | Medium | High |
|---|---|---|---|---|
| A: genes only | 49.354 | 13% | 22% | 47% |
| B: PSA + genes | 76.598 | 8% | 20% | 58% |
| C: Gleason + PSA | 111.441 | 3% | 22% | 58% |
| D: Final model[b] | 125.646 | 5% | 18% | 64% |

TABLE 7

| Primer Name | 5'-3' Sequence | description | SEQ ID NO: |
|---|---|---|---|
| VL.DPYS.F | GGTTTGGGGTGTTTTTTTGTAAGG | Forward primer | SEQ ID NO: 8 |
| VL.(B)DPYS.R | (B)-TAAACTCCAACCCAACCTTCC | Reverse primer | SEQ ID NO: 9 |
| VL.DPYS.s | AGTTTTGTTTTAGGTTGTAAATT | Sequencing primer | SEQ ID NO: 10 |
| CpG positions | YGGAGTTYGG YGGTTTGAYG GGTTTA | Sequence to analyse | SEQ ID NO: 11 |

TABLE 7-continued

| Primer Name | 5'-3' Sequence | description | SEQ ID NO: |
|---|---|---|---|
| Entire sequence amplified (converted DNA) | GGGTTATTTTTTAGAAAGTTGTATCGGTGTGGTTACGTTT AGCGTAGATATTTCGGGCGGTTTGTTAGTAGATGTAGGGG | | SEQ ID NO: 12 |
| VL.(8)-CCND2.F | (B)-GGGTTATTTTTTAGAAAGTTGTAT | Forward primer | SEQ ID NO: 13 |
| VL.CCND2.R | CCCCTACATCTACTAACAA | Reverse primer | SEQ ID NO: 14 |
| VL.CCND2.s | CCCTACATCTACTAACAAAC | Sequencing primer | SEQ ID NO: 15 |
| CpG positions | CRCCCRAAAT ATCTACRCTA AACRTAACCA CACCRATACA ACTTTCTAAA | Sequence to analyse | SEQ ID NO: 16 |
| Entire sequence amplified (converted DNA) | GGTTTGGGGTGTTTTTTTGTAAGGTTTTTATCGATAGTTT TCGAGTTTTGTTTTAGGTTGTAAATTCGGAGTTCGGCGGT TTGACGGGTTTATGATTTGGTCGTATATGCGGTTTTTTTT TTCGGGAAGGTTGGGTTGGAGTTTA | | SEQ ID NO: 17 |

The invention claimed is:

1. A detectably labelled nucleic acid molecule that hybridizes under stringent conditions in the vicinity of one of the genomic regions according to SEQ ID NO. 7, wherein said vicinity is any position having a distance of up to 1000 nucleotides from the 3'- or 5'-end of said genomic region and wherein said vicinity includes the genomic region itself, wherein the nucleic acid molecule is 40 to 180 nucleotides in length, and wherein the nucleic acid molecule:
   a) comprises one or more labels which are detectable by fluorescence or chemiluminescence;
   b) comprises one or more quencher molecules; and/or
   c) is a DNA analog comprising one or more of a 2-'O-alkyl sugar modification, a methylphosphonate, a phosphorothiate, a phosphorodithioate, a formacetal, a 3'-thioformacetal, a sulfone, a sulfamate, a nitroxide backbone modification, a base moiety modification, a morpholino analog, and peptide nucleic acid (PNA) analog.

2. The detectably labelled nucleic acid molecule of claim 1 wherein the nucleic acid molecule is 60-120 nucleotides in length.

3. The detectably labelled nucleic acid molecule of claim 1 wherein the detectably labelled nucleic acid molecule comprises one or more labels which are detectable by fluorescence or chemiluminescence.

4. The detectably labelled nucleic acid molecule of claim 1 wherein the nucleic acid molecule comprises one or more quencher molecules.

5. The detectably labelled nucleic acid molecule of claim 1 wherein the nucleic acid molecule is a DNA analog comprising one or more of a 2-'O-alkyl sugar modification, a methylphosphonate, a phosphorothiate, a phosphorodithioate, a formacetal, a 3'-thioformacetal, a sulfone, a sulfamate, a nitroxide backbone modification, a base moiety modification, a morpholino analog and peptide nucleic acid (PNA) analog.

6. The detectably labelled nucleic acid molecule of claim 1 wherein the detectably labelled nucleic acid molecule hybridizes under stringent conditions in the vicinity of one of the genomic regions after a bisulphite treatment of the genomic region.

7. A kit comprising the detectably labelled nucleic acid molecule of claim 1.

8. The kit of claim 7, in which the kit further comprises one or more nucleic acid molecules that hybridize under stringent conditions to at least one of the DPYS gene and the CCND2 gene.

* * * * *

SEQUENCE LISTING

<160> NUMBER OF SEQ ID NOS: 29

<210> SEQ ID NO 1
<211> LENGTH: 21
<212> TYPE: DNA
<213> ORGANISM: Artificial sequence
<220> FEATURE:
<223> OTHER INFORMATION: Synthetic sequence: Reverse primer
<220> FEATURE:
<221> NAME/KEY: misc_feature
<222> LOCATION: (1)..(1)
<223> OTHER INFORMATION: Linked to Biotin

<400> SEQUENCE: 1
caacctatct aactctatcc t                                           21

<210> SEQ ID NO 2
<211> LENGTH: 18
<212> TYPE: DNA
<213> ORGANISM: Artificial sequence
<220> FEATURE:
<223> OTHER INFORMATION: Synthetic sequence: Reverse primer
<220> FEATURE:
<221> NAME/KEY: misc_feature
<222> LOCATION: (1)..(1)
<223> OTHER INFORMATION: Linked to Biotin

<400> SEQUENCE: 2
cccctcccca tacactcc                                               18

<210> SEQ ID NO 3
<211> LENGTH: 26
<212> TYPE: DNA
<213> ORGANISM: Artificial sequence
<220> FEATURE:
<223> OTHER INFORMATION: Synthetic sequence: Reverse primer
<220> FEATURE:
<221> NAME/KEY: misc_feature
<222> LOCATION: (1)..(1)
<223> OTHER INFORMATION: Linked to Biotin

<400> SEQUENCE: 3
aatcattacc attaataaaa acctca                                      26

<210> SEQ ID NO 4
<211> LENGTH: 25
<212> TYPE: DNA

```
<213> ORGANISM: Artificial sequence
<220> FEATURE:
<223> OTHER INFORMATION: Synthetic sequence: Reverse primer
<220> FEATURE:
<221> NAME/KEY: misc_feature
<222> LOCATION: (1)..(1)
<223> OTHER INFORMATION: Linked to Biotin

<400> SEQUENCE: 4
tttttttgtt taggaattgg gagtg                                         25

<210> SEQ ID NO 5
<211> LENGTH: 19
<212> TYPE: DNA
<213> ORGANISM: Artificial sequence
<220> FEATURE:
<223> OTHER INFORMATION: Synthetic sequence: Reverse primer
<220> FEATURE:
<221> NAME/KEY: misc_feature
<222> LOCATION: (1)..(1)
<223> OTHER INFORMATION: Linked to Biotin

<400> SEQUENCE: 5
caaccccatc cccaaataa                                                19

<210> SEQ ID NO 6
<211> LENGTH: 21
<212> TYPE: DNA
<213> ORGANISM: Artificial sequence
<220> FEATURE:
<223> OTHER INFORMATION: Synthetic sequence: Reverse primer
<220> FEATURE:
<221> NAME/KEY: misc_feature
<222> LOCATION: (1)..(1)
<223> OTHER INFORMATION: Linked to Biotin

<400> SEQUENCE: 6
aatcaccatc ccaatcacct t                                             21

<210> SEQ ID NO 7
<211> LENGTH: 2240
<212> TYPE: DNA
<213> ORGANISM: Homo sapiens

<400> SEQUENCE: 7
tgcccagact ggtctcaaac tcctagcctc aagggaccct tctgccttgg cctcccaaag    60
tgctgagatt acaggcatga gccatgcacc cagccccttt ttaaaatttt tttgagagac   120
aagactttga tctgttgcct aggctggagt gcagtggtga gatcatagct cactgcagcc   180
tcaactcctg ggctcaagca ccagactcct tttatcacat tctatctcac acgcgtgtgg   240
ttccaatcct gcctctgcca cttctcagtt gtatgcccca acccaacctg tctggctctg   300
tcctccttaa cagaaggacg gccctggcca cgggccacag ccagcaacgc ttaagcacca   360
gggccggcga gtgccctgcc gtggcacggc tccagcgtcg cgctctcgaa ttcatttgct   420
ttccttaacg agagaaggtt ccagatgagg gctgaaccct cttcgccccg cccacggccc   480
ctgaacgctg ggggaggagt gcatgggagg ggcggccct caaacgggtc attgccatta    540
atagagacct caaacaccgc ctgctaaaaa tacccgactg gaggagcata aaagcgcagc   600
cgagcccagc gccccgcact tttctgagca gacgtccaga gcagagtcag ccagcatgac   660
cgagcgccgc gtcccttct cgctcctgcg ggccccagc tggaccccct tccgcgactg     720
gtacccgcat agccgcctct tcgaccaggc cttcgggctg cccggctgc ggaggagtg     780 gtcgcagtgg ttaggcggca gcagctggcc aggctacgtg cgcccctgc ccccgccgc    840
```

```
catcgagagc cccgcagtgg ccgcgcccgc ctacagccgc gcgctcagcc ggcaactcag      900
cagcggggtc tcggagatcc ggcacactgc ggaccgctgg cgcgtgtccc tggatgtcaa      960
ccacttcgcc ccggacgagc tgacggtcaa gaccaaggat ggcgtggtgg agatcaccgg     1020
tgagcccccc tgctcctgca ggggagagga ggaggctagc agggcgggca gggccggggg     1080
cgtgcggttg aaacgggggt cccgggggcc tggggagtta aacgttggcc cagcaccggg     1140
aaaaacagga ctcctgattc ccttgctcag gaattgggag tgcgggtcgc ttctaagggc     1200
gctttctgct ctgtaatccc agcgctttgg gaggccgaga cgggaggatc gcttgaggcc     1260
aggagttcaa gactagcctg gcaacatag cgagacgcgc ccccccgccc cgaccccgcg     1320
ccattacaaa aaaaaagcaa acaaaaattt ttttaaagat catcgatgaa gagagaaaat     1380
gcgcttttct acagagtccc cttcccaccc acagccccat cccagataa gcggggagtt     1440 ccctggcgcg gtgccagttt ctagccgctg agtgggcgtg tgcgcggctc caagtgcgcc     1500
tgcgtactgc tcactcccca gctccgcgcc ctgctccgtt cctcccaaaa ctctgaatcg     1560
aagaactttc cggaagtttc tgagagccca gaccggcggg cacgccccca tccccaaccc     1620
cctctgttaa tccctaccag cctgcagtcc tggctgcttc caagcaggag gtggggcctc     1680
tggcctagcg gggccgaaag gcagtcccct cccccgcagt ctgatttccc tcttccccccc    1740 aaaggcaagc acgaggagcg gcaggacgag catggctaca tctcccggtg cttcacgcgg     1800
aaatacacgt gagtcctggc gccaggtcgg ggtgggtggg tggcgtgggg gtggggtcag     1860
ggaagagggc acaggaccc acccggtgtg taatgtaacg cttgcctttc ctctctgcac      1920
gtccaggctg ccccccggtg tggaccccac ccaagtttcc tcctccctgt ccctgaggg     1980 cacactgacc gtggaggccc ccatgcccaa gctagccacg cagtccaacg agatcaccat     2040
cccagtcacc ttcgagtcgc gggcccagct tgggggccca gaagctgcaa aatccgatga     2100
gactgccgcc aagtaaagcc ttagcccgga tgcccacccc tgctgccgcc actggctgtg     2160
cctcccccgc cacctgtgtg ttcttttgat acatttatct tctgttttc tcaaataaag      2220 ttcaaagcaa ccacctgtca                                                 2240
```

<210> SEQ ID NO 8
<211> LENGTH: 24
<212> TYPE: DNA
<213> ORGANISM: Artificial sequence
<220> FEATURE:
<223> OTHER INFORMATION: Synthetic sequence: Forward primer

<400> SEQUENCE: 8

```
ggtttggggt gttttttttgt aagg                                            24
```

<210> SEQ ID NO 9
<211> LENGTH: 21
<212> TYPE: DNA
<213> ORGANISM: Artificial sequence
<220> FEATURE:
<223> OTHER INFORMATION: Synthetic sequence: Reverse primer
<220> FEATURE:
<221> NAME/KEY: misc_feature
<222> LOCATION: (1)..(1)
<223> OTHER INFORMATION: Linked to Biotin

<400> SEQUENCE: 9

```
taaactccaa cccaaccttc c                                                21
```

<210> SEQ ID NO 10

```
<211> LENGTH: 23
<212> TYPE: DNA
<213> ORGANISM: Artificial sequence
<220> FEATURE:
<223> OTHER INFORMATION: Synthetic sequence: Sequencing primer

<400> SEQUENCE: 10
agttttgttt taggttgtaa att                                              23

<210> SEQ ID NO 11
<211> LENGTH: 26
<212> TYPE: DNA
<213> ORGANISM: Homo sapiens

<400> SEQUENCE: 11
yggagttygg yggtttgayg ggttta                                           26

<210> SEQ ID NO 12
<211> LENGTH: 80
<212> TYPE: DNA
<213> ORGANISM: Homo sapiens

<400> SEQUENCE: 12
gggttatttt ttagaaagtt gtatcggtgt ggttacgttt agcgtagata tttcgggcgg      60
tttgttagta gatgtagggg                                                  80

<210> SEQ ID NO 13
<211> LENGTH: 24
<212> TYPE: DNA
<213> ORGANISM: Artificial sequence
<220> FEATURE:
<223> OTHER INFORMATION: Synthetic sequence: Forward primer
<220> FEATURE:
<221> NAME/KEY: misc_feature
<222> LOCATION: (1)..(1)
<223> OTHER INFORMATION: Linked to Biotin

<400> SEQUENCE: 13
gggttatttt ttagaaagtt gtat                                             24

<210> SEQ ID NO 14
<211> LENGTH: 19
<212> TYPE: DNA
<213> ORGANISM: Artificial sequence
<220> FEATURE:
<223> OTHER INFORMATION: Synthetic sequence: Reverse primer

<400> SEQUENCE: 14
cccctacatc tactaacaa                                                   19

<210> SEQ ID NO 15
<211> LENGTH: 20
<212> TYPE: DNA
<213> ORGANISM: Artificial sequence
<220> FEATURE:
<223> OTHER INFORMATION: Synthetic sequence: Sequencing primer

<400> SEQUENCE: 15
ccctacatct actaacaaac                                                  20

<210> SEQ ID NO 16
<211> LENGTH: 50
<212> TYPE: DNA
<213> ORGANISM: Homo sapiens

<400> SEQUENCE: 16
```

```
crcccraaat atctacrcta aacrtaacca caccrataca actttctaaa            50
```

<210> SEQ ID NO 17
<211> LENGTH: 145
<212> TYPE: DNA
<213> ORGANISM: Homo sapiens

<400> SEQUENCE: 17

```
ggtttggggt gtttttttgt aaggttttta tcgatagttt tcgagttttg ttttaggttg   60
taaattcgga gttcggcggt ttgacgggtt tatgatttgg tcgtatatgc ggttttttt  120 ttcgggaagg ttgggttgga gttta                                       145
```

<210> SEQ ID NO 18
<211> LENGTH: 23
<212> TYPE: DNA
<213> ORGANISM: Artificial sequence
<220> FEATURE:
<223> OTHER INFORMATION: Synthetic sequence: Forward primer

<400> SEQUENCE: 18

```
agttttatt tggaatttt ttt                                            23
```

<210> SEQ ID NO 19
<211> LENGTH: 21
<212> TYPE: DNA
<213> ORGANISM: Artificial sequence
<220> FEATURE:
<223> OTHER INFORMATION: Synthetic sequence: Sequencing primer

<400> SEQUENCE: 19

```
gttaaggaaa gtaaatgaat t                                            21
```

<210> SEQ ID NO 20
<211> LENGTH: 26
<212> TYPE: DNA
<213> ORGANISM: Artificial sequence
<220> FEATURE:
<223> OTHER INFORMATION: Synthetic sequence: Forward primer

<400> SEQUENCE: 20

```
agagaaggtt ttagatgagg gttgaa                                       26
```

<210> SEQ ID NO 21
<211> LENGTH: 18
<212> TYPE: DNA
<213> ORGANISM: Artificial sequence
<220> FEATURE:
<223> OTHER INFORMATION: Synthetic sequence: Sequencing primer

<400> SEQUENCE: 21

```
gatgagggtt gaattttt                                                18
```

<210> SEQ ID NO 22
<211> LENGTH: 21
<212> TYPE: DNA
<213> ORGANISM: Artificial sequence
<220> FEATURE:
<223> OTHER INFORMATION: Synthetic sequence: Forward primer

<400> SEQUENCE: 22

```
ggttatgttg gttgattttg t                                            21
```

<210> SEQ ID NO 23

<211> LENGTH: 19
<212> TYPE: DNA
<213> ORGANISM: Artificial sequence
<220> FEATURE:
<223> OTHER INFORMATION: Synthetic sequence: Sequencing primer

<400> SEQUENCE: 23
tggttgattt tgttttgga                                                    19

<210> SEQ ID NO 24
<211> LENGTH: 23
<212> TYPE: DNA
<213> ORGANISM: Artificial sequence
<220> FEATURE:
<223> OTHER INFORMATION: Synthetic sequence: Forward primer

<400> SEQUENCE: 24
atcttaaact cctaacctca aac                                               23

<210> SEQ ID NO 25
<211> LENGTH: 20
<212> TYPE: DNA
<213> ORGANISM: Artificial sequence
<220> FEATURE:
<223> OTHER INFORMATION: Synthetic sequence: Sequencing primer

<400> SEQUENCE: 25
tttgtttagg aattgggagt                                                   20

<210> SEQ ID NO 26
<211> LENGTH: 18
<212> TYPE: DNA
<213> ORGANISM: Artificial sequence
<220> FEATURE:
<223> OTHER INFORMATION: Synthetic sequence: Forward primer

<400> SEQUENCE: 26
agttggggag tgagtagt                                                     18

<210> SEQ ID NO 27
<211> LENGTH: 16
<212> TYPE: DNA
<213> ORGANISM: Artificial sequence
<220> FEATURE:
<223> OTHER INFORMATION: Synthetic sequence: Sequencing primer

<400> SEQUENCE: 27
tggggagtga gtagta                                                       16

<210> SEQ ID NO 28
<211> LENGTH: 26
<212> TYPE: DNA
<213> ORGANISM: Artificial sequence
<220> FEATURE:
<223> OTHER INFORMATION: Synthetic sequence: Forward primer

<400> SEQUENCE: 28
attttgtagt ttttgggttt ttaagt                                            26

<210> SEQ ID NO 29
<211> LENGTH: 20
<212> TYPE: DNA
<213> ORGANISM: Artificial sequence
<220> FEATURE:
<223> OTHER INFORMATION: Synthetic sequence: Sequencing primer

```
<400> SEQUENCE: 29
tttgggtttt taagttgggt                                          20
```